(12) United States Patent
Thyagarajan

(10) Patent No.: US 6,589,570 B1
(45) Date of Patent: Jul. 8, 2003

(54) PHARMACEUTICAL FORMULATION USEFUL FOR THE TREATMENT OF HEPATITIS B, HEPATITIS C AND OTHER VIRAL INFECTIONS OF THE LIVER AND A PROCESS FOR ITS PREPARATION

(75) Inventor: Sadras Panchatcharam Thyagarajan, Chennai (IN)

(73) Assignee: University of Madras, Chennai (IN)

( * ) Notice: Subject to any disclaimer, the term of this patent is extended or adjusted under 35 U.S.C. 154(b) by 0 days.

(21) Appl. No.: 09/719,486

(22) PCT Filed: Apr. 10, 2000

(86) PCT No.: PCT/IN00/00046

§ 371 (c)(1),
(2), (4) Date: Dec. 12, 2000

(87) PCT Pub. No.: WO00/61161

PCT Pub. Date: Oct. 19, 2000

(30) Foreign Application Priority Data

Apr. 12, 1999 (IN) ................................................. 405/99

(51) Int. Cl.⁷ .............................................. A61K 35/78
(52) U.S. Cl. ....................... 424/725; 424/773; 424/774; 424/776; 424/779
(58) Field of Search ................................ 424/725, 773, 424/774, 776, 779

(56) References Cited

FOREIGN PATENT DOCUMENTS

| EP | 0 890 360 A1 | 1/1999 |
| WO | WO 00/56347 | 9/2000 |

OTHER PUBLICATIONS

Moshi et al. A study of the effects of *phyllanthus amarus* extracts on blood in rabbits (Jul. 1997) International Journal of Pharmacognosy, vol. 35, No. 3, pp. 167–173.*

Calixto et al. A review of the plants of the genus phylanthus: their chemistry, pharmacology, and therapeutic potential (1998) Med. Res. Rev., vol. 18, No. 4, pp. 225–258.*

Abstract (Accession No. PREV199395195864 XP–002151737) for Sheau–Farn, Yeh, et al., "Effect of an extract from *Phyllanthus amarus* on heptatitis B surface antigen gene expression in human hepatoma cells," *Antiviral Research*, vol. 20, No. 3, pp. 185–192 (1993).

Mehrotra, R., et al., "In vitro effect of *Phyllanthus amarus* on hepatitis B virus," *Indian Journal of Medical Research* [A] 93, pp. 71–73 (1991).

Abstract (PREV199698559653 XP–002151738) for Wang, Meixia, et al., "Herbs of the genus Phyllanthus in the treatment of chronic hepatitis B: Observations with three preparations from different geographic sites," *Journal of Laboratory and Clinical Medicine*, vol. 126, No. 4, pp. 350–352 (1995).

\* cited by examiner

Primary Examiner—Leon B. Lankford, Jr.
Assistant Examiner—Susan D. Coe
(74) Attorney, Agent, or Firm—Ladas & Parry

(57) ABSTRACT

The invention disclosed in this application relates to a pharmaceutical formulation prepared from the biotyped variety of the medicinal plant, *Phyllanthus amarus* which is useful for the treatment of Hepatitis B (both acute and chronic), Hepatitis C (both acute and chronic) and other related viral infections of the liver with antihepatotoxic and liver cell regenerating potentials and immunomodulating properties. The invention confirms, that when pars of the biotyped variety of the medicinal plant, *Phyllanthus amarus* are extraceted separately with a polar solvent alone, polar solvent and water in specific ratios and water alone and when such extracts are mixed together, the resultant formulation has all the essential antiviral and biological properties, while the individual polar or aqueous extracts alone does not possess one or more of these properties. The present invention also relates to a process for the preparation of the above said new pharmaceutical formulation with biological and chemical standardisation protocols.

30 Claims, 10 Drawing Sheets

```
PC MC MS SO PP MO CA PR E           <PC> Peak-top Comments
C-R4A CHROMATOPAC    CH=1    REPORT No.=2    CHROMATOGRAM=1:@CHRM1.C76    99/02/15  10:06:01
Analysis File : 1:@FILE1
** CALCULATION REPORT **
CH PKNO   TIME      AREA      HEIGHT    MK  IDNO     CONC       NAME
 1   1    0.167     18233       413                  0.9329
     2    1.018      4453       407     V            0.2279
     3    1.877    260130     17023     V           13.3094
     4    2.436     53756      6892     V            2.7504
     5    2.825      4891       700     V            0.2502
     6    2.995     22666       755     V            1.1597
     7    3.528     16446       735     V            0.8414
     8    3.878     18492       701     V            0.9461
     9    4.353     14456       660     V            0.7396
    10    4.738     12572       668     V            0.6432
    11    5.601     71795       931     V            3.6733
    12    9.837    271522      2879     V           13.8923
    13   10.247     68388      1167     V            3.499
    14   13.548    426941      3067     V           21.8442
    15   15.694     88106      1613                  4.5079
    16   17.174    201434      1354     V           10.3062
    17   20.172    113040      1334     V            5.7836
    18   21.689     40338       823     V            2.0639
    19   23.325     90602       971     V            4.6356
    20   26.118    139062       710     V            7.115
    21   28.265     17164       314     V            0.8782
                 ----------  --------                ---------
         TOTAL   1954486     44117                   100
```

PC MC MS SO PP MO CA PR E                  <PC> Peak-top Comments
C-R4A CHROMATOPAC   CH-1   REPORT No. = 3    CHROMATOGRAM = 1:@CHRM1.C75    99.02.12    12:43:37
 CALCULATION REPORT

| CH | PK NO | TIME | AREA | HEIGHT | MK | INDO | CONC | NAME |
|---|---|---|---|---|---|---|---|---|
| 1 | 1 | 1.037 | 9990 | 113 | | | 0.8222 | |
| | 2 | 2.149 | 3372 | 144 | | | 0.2776 | |
| | 3 | 2.429 | 2383 | 162 | V | | 0.1962 | |
| | 4 | 2.684 | 494 | 59 | | | 0.0407 | |
| | 5 | 5.239 | 663121 | 10971 | V | | 54.5816 | |
| | 6 | 5.914 | 5598 | 1669 | | | 0.4607 | |
| | 7 | 7.212 | 24533 | 1237 | V | | 2.0193 | |
| | 8 | 8.789 | 45556 | 1834 | | | 3.7497 | |
| | 9 | 9.476 | 64921 | 1324 | V | | 53437 | |
| | 10 | 11.602 | 22766 | 697 | | | 1.8739 | |
| | 11 | 13.704 | 122955 | 1841 | V | | 10.1284 | |
| | 12 | 15.859 | 53848 | 794 | V | | 4.3664 | |
| | 13 | 18.823 | 75870 | 740 | V | | 6.2449 | |
| | 14 | 20.957 | 24782 | 303 | V | | 2.0398 | |
| | 15 | 21.839 | 10377 | 327 | V | | 0.8541 | |
| | 16 | 22.855 | 28411 | 410 | V | | 2.3385 | |
| | 17 | 26.058 | 32309 | 467 | V | | 2.6593 | |
| | 18 | 29.442 | 24431 | 490 | | | 2.0109 | |
| | | TOTAL | 1214916 | 22781 | | | 100 | |

PC MC MS SO PP MO CA PR E                            <PC> Peak-top Comments C-R4A CHROMATOPAC CH-1 REPORT No. = 2 CHROMATOGRAM = 1:@CHRM1.C64    99.02.09    15:03:28

\*\* CALCULATION REPORT\*\*

| CH | PK NO | TIME | AREA | HEIGHT | MK | INDO | CONC | NAME |
|---|---|---|---|---|---|---|---|---|
| 1 | 1 | 0.375 | 1113 | 90 | | | 0.0252 | |
| | 2 | 0.958 | 40336 | 720 | | | 0.9119 | |
| | 3 | 3.653 | 831417 | 18416 | VE | | 18.7958 | |
| | 4 | 5.263 | 271922 | 4798 | E | | 6.1473 | |
| | 5 | 6.425 | 287619 | 5234 | V | | 6.5022 | |
| | 6 | 7.654 | 400784 | 4324 | V | | 9.0605 | |
| | 7 | 9.075 | 188959 | 4009 | V | | 4.2718 | |
| | 8 | 10.192 | 379882 | 4232 | V | | 8.588 | |
| | 9 | 11.703 | 229913 | 3446 | V | | 5.1976 | |
| | 10 | 12.775 | 118068 | 3264 | V | | 2.6692 | |
| | 11 | 13.212 | 172084 | 3176 | V | | 3.8903 | |
| | 12 | 14.037 | 240926 | 3012 | V | | 5.4466 | |
| | 13 | 16.26 | 495904 | 2798 | V | | 11.2109 | |
| | 14 | 18.642 | 106571 | 2134 | V | | 2.4092 | |
| | 15 | 20.086 | 141461 | 2044 | V | | 3.198 | |
| | 16 | 20.806 | 79389 | 1727 | V | | 1.7947 | |
| | 17 | 22.177 | 206128 | 1831 | V | | 4.6599 | |
| | 18 | 24.281 | 120736 | 1320 | V | | 2.7295 | |
| | 19 | 27.28 | 75691 | 529 | V | | 1.7111 | |
| | 20 | 28.631 | 34513 | 398 | V | | 0.7802 | |
| | | TOTAL | 4423414 | 67502 | | | 100 | |

```
PC MC MS SO PP MO CA PR E              <PC> Peak-top Comments
C-R4A CHROMATOPAC    CH=1    REPORT No.=5    CHROMATOGRAM=1:@CHRM1.C63    99/02/08  12:06:34

Analysis File : 1:@FILE1
```

```
 CALCULATION REPORT 
CH PKNO   TIME      AREA     HEIGHT   MK  IDNO    CONC        NAME
 1   1    1.56      24552      914                0.838
     2    2.15      31823     1081    V           1.0861
     3    3.806    396657    12404    V          13.5382
     4    4.839    164696     3318                5.6212
     5    5.924    169940     2930    V           5.8002
     6    7.466    244520     2921    V           8.3457
     7    8.674    240990     2980    V           8.2252
     8    9.957    112405     2658    V           3.8365
     9   11.322    316776     2461    V          10.8118
    10   13.275    113119     2218    V           3.8608
    11   13.815     91360     2117    V           3.1182
    12   14.46     130731     1988    V           4.462
    13   15.624     93697     1831    V           3.1979
    14   16.767    133126     2016    V           4.5437
    15   18.127     83247     1577    V           2.8413
    16   19.197    195454     1833    V           6.671
    17   21.407     84345     1186    V           2.8788
    18   22.139     48895     1011    V           1.6688
    19   23.447     61796     1095    V           2.1091
    20   25.276    127645     1015    V           4.3566
    21   26.95      42554      584    V           1.4524
    22   28.546     21583      424                0.7367
                  --------   ------              --------
         TOTAL    2929908    50560                100
```

```
PC MC MS SO PP MO CA PR E           <PC> Peak-top Comments
C-R4A CHROMATOPAC    CH=1    REPORT No.=3   CHROMATOGRAM=1:@CHRM1.C67    99/02/10  15:33:43

Analysis File : 1:@FILE1
```

```
 CALCULATION REPORT 
CH  PKNO   TIME     AREA      HEIGHT    MK  IDNO     CONC       NAME
 1    1   0.083       267        49                  0.0119
      2   2.183     13316       613                  0.5941
      3   3.139    132750      4265                  5.9224
      4   4.178    335522     13555                 14.9687
      5   4.734      7783       769                  0.3472
      6   5.784     86812      3464                  3.873
      7   6.159     36059      2382    V             1.6087
      8   6.522    108520      2585    V             4.8414
      9   7.556    107203      2697    V             4.7827
     10   8.59     146833      2744    V             6.5507
     11   9.336     69597      2222    V             3.1049
     12   9.758    113737      2345    V             5.0742
     13  10.585    128299      2010    V             5.7238
     14  12.474    120696      1985    V             5.3846
     15  13.192    178658      1957    V             7.9705
     16  17.48     373297      1349    V            16.654
     17  19.353     34633      1004    V             1.5451
     18  20.938    122545      1067    V             5.4671
     19  22.286     28797       672    V             1.2847

20  23.539     38284       571    V             1.708
     21  25.565     50635       328    V             2.259
     22  27.824      7247        63    V             0.3233
                  ---------  --------              ---------
         TOTAL    2241488     48693                  100
```

```
MC MS SO PP MO CA PR E        <PC> Peak-top Comments
C-R4A CHROMATOPAC    CH=1    REPORT No.=4    CHROMATOGRAM=1:@CHRM1.C69    99/02/11  12:04:02

Analysis File : 1:@FILE1
```

CALCULATION REPORT

| CH | PKNO | TIME | AREA | HEIGHT | MK | IDNO | CONC | NAME |
|----|------|------|------|--------|----|----|------|------|
| 1 | 1 | 0.57 | 15572 | 236 | | | 0.5245 | |
| | 2 | 3.942 | 492061 | 13065 | | | 16.574 | |
| | 3 | 4.234 | 7342 | 756 | | | 0.2473 | |
| | 4 | 4.562 | 50510 | 1880 | | | 1.7013 | |
| | 5 | 5.562 | 142045 | 3086 | | | 4.7845 | |
| | 6 | 7.166 | 159866 | 3144 | V | | 5.3847 | |
| | 7 | 7.789 | 95247 | 2677 | V | | 3.2082 | |
| | 8 | 8.599 | 109771 | 2827 | V | | 3.6974 | |
| | 9 | 8.916 | 183793 | 2928 | V | | 6.1907 | |
| | 10 | 10.559 | 179376 | 2665 | V | | 6.0419 | |
| | 11 | 11.589 | 158257 | 2659 | V | | 5.3306 | |
| | 12 | 12.252 | 117273 | 2266 | V | | 3.9501 | |
| | 13 | 14.257 | 191373 | 2183 | V | | 6.446 | |
| | 14 | 15.014 | 114958 | 1993 | V | | 3.8721 | |
| | 15 | 16.366 | 136277 | 1875 | V | | 4.5902 | |
| | 16 | 18.217 | 266283 | 1950 | V | | 8.9692 | |
| | 17 | 20.067 | 74176 | 1408 | V | | 2.4984 | |
| | 18 | 21.4 | 220972 | 1747 | V | | 7.443 | |
| | 19 | 23.627 | 51892 | 997 | V | | 1.7479 | |
| | 20 | 24.849 | 75039 | 893 | V | | 2.5275 | |
| | 21 | 26.758 | 118084 | 1023 | V | | 3.9774 | |
| | 22 | 28.888 | 8700 | 402 | | | 0.2931 | |
| | | TOTAL | 2968867 | 52659 | | | 100 | |

```
PC MC MS SO PP MO CA PR E            <PC> Peak-top Comments
C-R4A CHROMATOPAC    CH=1    REPORT No.=1    CHROMATOGRAM=1:@CHRM1.C65    99/02/09  16:02:53

Analysis File : 1:@FILE1
```

CALCULATION REPORT

| CH | PKNO | TIME | AREA | HEIGHT | MK | IDNO | CONC | NAME |
|---|---|---|---|---|---|---|---|---|
| 1 | 1 | 0.473 | 28591 | 739 | | | 0.6621 | |
| | 2 | 1.646 | 10020 | 958 | | | 0.232 | |
| | 3 | 3.317 | 806145 | 14547 | VE | | 18.6681 | |
| | 4 | 5.136 | 179994 | 5030 | | | 4.1682 | |
| | 5 | 5.974 | 171127 | 5161 | V | | 3.9628 | |
| | 6 | 6.4 | 210063 | 5268 | V | | 4.8645 | |
| | 7 | 7.148 | 99411 | 4295 | V | | 2.3021 | |
| | 8 | 7.975 | 194665 | 3679 | V | | 4.5079 | |
| | 9 | 8.793 | 203648 | 4460 | V | | 4.7159 | |
| | 10 | 9.457 | 178132 | 4229 | V | | 4.125 | |
| | 11 | 10.192 | 93670 | 3730 | V | | 2.1691 | |
| | 12 | 10.776 | 419825 | 4127 | V | | 9.722 | |
| | 13 | 12.816 | 161070 | 3325 | V | | 3.7299 | |
| | 14 | 14.823 | 521812 | 3424 | V | | 12.0837 | |
| | 15 | 16.793 | 181695 | 2643 | V | | 4.2075 | |
| | 16 | 17.66 | 116529 | 2316 | V | | 2.6985 | |
| | 17 | 18.908 | 195783 | 2343 | V | | 4.5338 | |
| | 18 | 20.263 | 134488 | 1938 | V | | 3.1144 | |
| | 19 | 21.594 | 102152 | 1549 | V | | 2.3655 | |
| | 20 | 22.644 | 59025 | 1375 | V | | 1.3668 | |
| | 21 | 24.713 | 179567 | 1560 | V | | 4.1583 | |
| | 22 | 25.808 | 26551 | 314 | V | | 0.6148 | |
| | 23 | 27.144 | 22506 | 513 | V | | 0.5212 | |
| | 24 | 27.756 | 8233 | 365 | V | | 0.1906 | |
| | 25 | 28.275 | 9080 | 261 | V | | 0.2103 | |
| | 26 | 28.875 | 4530 | 164 | V | | 0.1049 | |
| | | TOTAL | 4318306 | 78314 | | | 100 | |

PC MC MS SO PP MO CA PR E           \<PC\> Peak-top Comments
C-R4A CHROMATOPAC CH-1 REPORT No. = 2 CHROMATOGRAM = 1:@CHRM1.C36    99/02/24   09:03:36
 CALCULATION REPORT

| CH | PK NO | TIME | AREA | HEIGHT | MK | INDO | CONC | NAME |
|---|---|---|---|---|---|---|---|---|
| 1 | 1 | 0.317 | 2933 | 92 | | | 0.0962 | |
| | 2 | 1.714 | 25970 | 299 | V | | 0.8519 | |
| | 3 | 3.887 | 551431 | 13840 | V | | 18.0889 | |
| | 4 | 4.407 | 16583 | 1091 | | | 0.544 | |
| | 5 | 4.634 | 24561 | 1199 | V | | 0.8057 | |
| | 6 | 5.175 | 7792 | 969 | | | 0.2556 | |
| | 7 | 5.941 | 68791 | 3481 | | | 2.2566 | |
| | 8 | 6.597 | 128163 | 3311 | V | | 4.2042 | |
| | 9 | 7.551 | 163905 | 3358 | V | | 5.3767 | |
| | 10 | 8.135 | 86289 | 2946 | V | | 2.8306 | |
| | 11 | 9.361 | 245548 | 3047 | V | | 8.0548 | |
| | 12 | 10.752 | 309416 | 3796 | V | | 10.1499 | |
| | 13 | 12.546 | 250642 | 2995 | V | | 8.2219 | |
| | 14 | 13.698 | 102576 | 2518 | V | | 3.3649 | |
| | 15 | 15.603 | 305161 | 2555 | V | | 10.0104 | |
| | 16 | 17.237 | 192929 | 2458 | V | | 6.3288 | |
| | 17 | 18.89 | 235216 | 1883 | V | | 7.7159 | |
| | 18 | 22.408 | 234219 | 2916 | V | | 7.6832 | |
| | 19 | 25.046 | 42344 | 914 | | | 1.389 | |
| | 20 | 26.7 | 5247 | 85 | V | | 0.1721 | |
| | 21 | 27.521 | 48739 | 1052 | | | 1.5988 | |
| | | TOTAL | 3049453 | 54803 | | | 100 | |

PC MC MS SO PP MO CA PR E      <PC> Peak-top Comments
    CALCULATION REPORT        97.03.29     16:11:35

| CH | PK NO | TIME | AREA | HEIGHT | MK | INDO | CONC | NAME |
|----|-------|------|------|--------|----|------|------|------|
| 1 | 1 | 2.214 | 26238 | 823 | | | 6.1297 | |
| | 2 | 2.732 | 68384 | 4371 | SV | | 15.9759 | |
| | 3 | 3.383 | 199 | 17 | T | | 0.0466 | |
| | 4 | 4.433 | 145 | 6 | T | | 0.0339 | |
| | 5 | 5.4 | 43 | 4 | T | | 0.0101 | |
| | 6 | 6.371 | 81 | 5 | T | | 0.019 | |
| | 7 | 8.476 | 11458 | 527 | | | 2.6768 | |
| | 8 | 9.103 | 5146 | 174 | V | | 1.2021 | |
| | 9 | 13.431 | 56914 | 338 | V | | 13.2962 | |
| | 10 | 14.533 | 17485 | 315 | V | | 4.0847 | |
| | 11 | 16.724 | 118858 | 1198 | V | | 27.7677 | |
| | 12 | 20.519 | 23182 | 268 | V | | 5.4157 | |
| | 13 | 21.933 | 5004 | 182 | V | | 1.169 | |
| | 14 | 23.8 | 61774 | 284 | V | | 14.4316 | |
| | 15 | 26.794 | 33135 | 280 | V | | 7.741 | |
| | | TOTAL | 428044 | 8792 | | | 100 | |

CALCULATION REPORT                    97.03.29        13:29:55

| CH | PK NO | TIME | AREA | HEIGHT | MK | INDO | CONC | NAME |
|----|-------|------|------|--------|----|------|------|------|
| 1  | 1     | 2.075 | 46869 | 1391 |    |      | 8.983 |     |
|    | 2     | 2.587 | 78622 | 4474 | SV |      | 15.0687 |   |
|    | 3     | 4.169 | 39    | 5    | T  |      | 0.0074 |    |
|    | 4     | 4.375 | 177   | 8    | TV |      | 0.0339 |    |
|    | 5     | 5.208 | 23    | 2    | T  |      | 0.0045 |    |
|    | 6     | 12.308 | 37146 | 293 |    |      | 7.1194 |    |
|    | 7     | 16.445 | 207693 | 1691 | V |      | 39.8064 |  |
|    | 8     | 20.036 | 28606 | 289 | V  |      | 5.4826 |    |
|    | 9     | 25.41 | 87883 | 386  | V  |      | 16.8437 |   |
|    | 10    | 26.675 | 34699 | 324 | V  |      | 6.6504 |    |
|    |       | TOTAL | 521757 | 8863 |   |      | 100    |    |

PHARMACEUTICAL FORMULATION USEFUL FOR THE TREATMENT OF HEPATITIS B, HEPATITIS C AND OTHER VIRAL INFECTIONS OF THE LIVER AND A PROCESS FOR ITS PREPARATION

TECHNICAL FIELD

This invention relates to a pharmaceutical formulation useful for the treatment of Hepatitis B and Hepatitis C and other viral infections of liver. This invention particularly relates to a pharmaceutical formulation useful for the treatment of acute and chronic Hepatitis B & C virus infections prepared from the Indian biotyped medicinal plant, *Phyllanthus amarus*. This invention also relates to a process for the preparation of the pharmaceutical formulation useful for the treatment of acute and chronic Hepatitis B and Hepatitis C and other viral infections of the liver from the medicinal plant *Phyllanthus amarus*.

It is needless to stress the need for a s drug that would keep the liver functioning at its optimum or the one that would be selectively active against the currently known etiological agents of acute and chronic viral diseases of the liver. This is important because the disease of the liver throw the entire human body out of gear. The exciting alphabet of viral Hepatitis includes a wide range of totally unrelated often highly unusual pathogenic human viruses like Hepatitis A virus (HAV), Hepatitis B virus (HSV), Hepatitis C virus (HCV), Hepatitis D virus (HDV), Hepatits E virus (HEV) etc. Of the viruses it has been clearly established that HBV, HCV and HDV are the ones that are associated with the development of chronic persistent/active hepatitis, cirrhosis of the liver and even hepatocellular carcinoma besides being associated with fulminant hepatitis and sub acute hepatic failure.

BACKGROUND ART

Acute and Chronic Hepatitis-B

The natural disease course in HBV is being summarized to understand the need for the effective management and treatment of Hepatitis B in a country. For normal adults with low viral production and an early immune response, the disease course is self limiting and usually asymptomatic (60–80% of all HBV infections). Individuals who replicate the virus in larger quantities, with a relatively late immune response have a self-limiting symptomatic acute hepatitis. Irrespective of whether initially symptomatic or asymptomatic, the infection becomes chronic in 5–10% of the individuals, 20–30% of them developing clinical sequelae such as chronic hepatitis, cirrhosis or hepatoma within years or decades. In neonates, however, the immune defence is still lacking (induction of tolerance), so that infected individuals do not develop acute hepatitis, but more of them become chronic camers (80–90%). Such carriers also progress frequently to chronic clinical sequelae faster. Between these two extremes are immunocompromised individuals, such as intravenous drug users, haemodialysis patients or transplant recipients, who are more likely to become chronic carriers than are healthy adults (10–60%). (WHO Tech. Report Series 1987;754:18).

Based on substantial body of data, HBV has been proved as a major pathogen producing chronic liver diseases. It has also been proved that there are over 400 million healthy carriers of HBV all over the world and one tenth of these carriers (40 millions) being in India alone. These carriers besides acting as human reservoirs of HBV infection also act as primary source of spread of HBV infection to the community and was also shown to have 200 times increased risk of developing chronic liver diseases and/or hepatocellular carcinoma.

With the above documented international HBV scenario, the HBV epidemiology in India is to be considered as alarming since there are definite data on prevalence pattern of HBV in asymptomatic population (4%) high risk groups (13%), significant involvement of HBV in Indian acute and sub-acute liver failure cases (42 & 45%). 70% of the chronic hepatitis cases, 40–80% of cirrhosis cases and over 60% of primary liver cancer cases.

Although effective vaccines have been developed against HBV and successfully adopted, the need for effective treatment of acute and chronic Hepatitis B has become universal public health emergency since vaccines as on date are neither capable of inducing immunity in a carrier nor able to eliminate HBV carrier status. Research conducted from the mid 70s have delineated several agents to have treatment potential in chronic HBV infections which has been illustrated in the Table 1 given below.

TABLE 1

Agents that have been studied in the treatment of HBV infection (Lau et al., Gut. Suppl. 1991;547–562)

| Anti-virals | Immunosuppressive | Immunostimulators |
| --- | --- | --- |
| Interferons | Corticosteroids | BCG vaccination |
| Alpha interferon | | Levamisole |
| Beta interferon | | Interleukin-2 |
| Gamma interferon | | Interferon gamma |
| Tumour necrosis factor | | Thymosin |
| Adenine arabinoside (Ara-A) | | Tumor necrosis |
| Acyclovir, deoxyacyclovir | | factor |
| Zidovudine | | |
| Suramin | | |
| Ribavirin | | |
| Phosphonoformate | | |
| Quinacrine | | |
| (+)-cyanidanol-3 | | |
| Lamuvidine | | |
| Phyllanthus amarus | | |

However, except the interferons, Lamuvidine and the latest entry *Phyllanthus amarus*, the others seem to be far from successful. The limited success rate, prohibitive cost, profound side effects and the non-accessibility of interferons and Lamuvidine in developing and underdeveloped counties have necessitated further search for newer antihepatitis B agents.

Acute and Chronic Hepatitis-C

1. Acute HCV Infection

Persons with acute HCV infection typically are either asymptomatic or have a mild clinical illness; 60%–70% have no discernible symptoms; 20%–30% might have jaundice; and 10%–20% might have nonspecific symptoms (e.g. anorexia, malaise or abdominal pain). Clinical illness in patients with acute hepatitis C who seek medical care is similar to that of other types of viral hepatitis, and serologic testing is necessary to determine the etiology of hepatitis in an individual patient. In $\geq 20\%$ of these patients, onset of symptoms might precede anti-HCV seroconversion. Average time period from exposure to symptom onset is 6–7 weeks, whereas average time period from exposure to seroconversion is 8–9 weeks. Anti-HCV can be detected in 80% of patients within 15 weeks after exposure, in $\geq 90\%$ within 5 months after exposure, and in $\geq 97\%$ by 6 months after exposure. Rarely, seroconversion might be delayed until 9 months after exposure.

The course of acute hepatitis C is variable, although elevations in serum ALT levels often in a fluctuating pattern, are its most characteristic feature. Normalization of ALT levels might occur and suggests full recovery, but this is frequently followed by ALT elevations that indicate progression to chronic disease. Fulminant hepatic failure following acute hepatitis C is rare. However, in developing country especially India, HCV in FHF was reported significantly.

2. Chronic HCV Infection

After acute infection, 15%–25% of persons appear to resolve their infection without sequelae as defined by substained absence of HCV RNA in serum and normalization of ALT levels. Chronic HCV infection develops in most persons (75%–85%), with persistent or fluctuating ALT elevations indicating active liver disease developing in 60%–70% of chronically infected persons. In the remaining 30%–40% of chronically infected persons, ALT levels are normal. No clinical or epidemiologic features among patients with acute infection have been found to be predictive of either persistent infection or chronic liver disease. Moreover, various ALT patterns have been observed in these patients during follow-up, and patients might have prolonged periods ($\geq 12$ months) of normal ALT activity even though they have histologically confirmed chronic hepatitis. Thus a single ALT determination cannot be used to exclude ongoing hepatic injury, and long term follow-up of patients with HCV infection is required to determine their clinical outcome or prognosis.

The course of chronic liver disease is usually insidious, progressing at a slow rate without symptoms or physical signs in the majority of patients during the first two or more decades after infection. Frequently, chronic hepatitis C is not recognised until asymptomatic persons are identified as HCV positive during blood donor screening or elevated ALT levels are detected during routine physical examinations. Most studies have reported that cirrhosis develops in 10%–20% of persons with chronic hepatitis C over a period of 20–30 years, and HCC in 1%–5%, with striking geographic variations in rates of this disease. This difference is more discernable also in the SEA region countries.

Although factors predicting severity of liver disease have not been well defined, recent data indicate that increased alcohol intake, being aged >40 years at infection, and being male are associated with more severe liver disease. In particular, among persons with alcoholic liver disease and HCV infection, liver disease progresses more rapidly; among those with cirrhosis, a higher risk for development of HCC exists. Furthermore, even intake of moderate amounts (>10 g/day) of alcohol in patients with chronic hepatitis C might enhance disease progression. More severe liver injury observed in persons with alcoholic liver disease and HCV infection possibly is attributable to alcohol induced enhancement of viral replication or increased susceptibility of cells to viral injury.

The current treatment guidelines of HCV infection are presented below:

Current effective therapy for HCV infection is IFN based, with or without other therapeutic agents such as ribavirin. Ribavirin monotherapy is not recommended.

For the interim, patients with acute hepatitis should receive IFN-α, 3–6 million units (or 9–15 µg) thrice weekly for at least 6 months until more effective regimens emerge.

The standard treatment for previously untreated (naïve) patients with chronic hepatitis C is IFN-α, 36 million units (or 915 µg) thrice weekly for 12 months. However, recent data indicate that a regimen of IFN-α and ribavirin for 6 months or IFN-α monotherapy using different schedules and/or higher doses may significantly improve sustained response rates and become preferred options for treatment in the future.

Adverse sideeffects to IFN and ribavirin are tolerable, but a fatal outcome (suicide, liver failure, sepsis) has been observed primarily in patients with cirrhosis. Less severe side effects occur in less than 10% of the treated patients and include flu-like symptoms, fatigue, thinning of hair, myalgia, bone marrow suppression requiring dose reduction, neuropsychiatric effects, such as depression and autoimmune disease (thyroid). All patients must be carefully monitored by the prescribing doctor for side-effects by using appropriate.

biochemical, haematological and immunological tests. Appropriate medical records should be maintained.

Newer Search of Antiviral Agents Against Hepatitis B and Hepatitis C

One of these searches for the last two decades has been in the development of a promising antiviral agent against hepatitis B and hepatitis C and other viral infections of liver from the plant, *Phyllanthus amarus.*

*Phyllanthus niruri* Linn. as it has been indexed in majority of published ethano botanical reviews, until recently, belongs to the family Euphorbiaceae. Phyllanthus is one of the largest genera of the family Euphorbiaceae containing about 700 species. It has been shown that about 24 species of Phyllanthus are active against clinical Hepatits (jaundice) as indicated in Table 2, out of which 8 have been used in India.

TABLE 2

List of Phyllanthus species used in clinical jaundice
(Unander et al., J Ethnopharmacol 1991;34:97–133)

1. *Phyllanthus niruri*
2. *P. amarus*
3. *P. fraternus*
4. *P. mimicus*
5. *P. debilis*
6. *P. urinaria*
7. *P. caroliniemsis*
8. *P. abnormis*
9. *P. airy-shavii*
10. *P. tenellus*
11. *P. gasstroemi*
12. *P. gunni*
13. *P. similus*
14. *P. thymodes*
15. *P. hirtellus*
16. *P. stipulatus*
17. *P. niruroides*
18. *P. rheedi*
19. *P. acutifolius*
20. *P. hutchinosolianus*
21. *P. cantoniensis*
22. *P. virgatus*
23. *P. corcovadensis*
24. *P. palanessis*

Taxonomy of *Phyllanthus Amarus*

This plant has recently been delineated as a mixture of three distinct species namely *Phyllanthus amarus, Phyllanthus fraternus* and *Phyllanthus debilis.* It was later identified that the cirumtropical weed *P. amarus* is the predominant species in South India, particularly in Tamilnadu. *P. amarus* are erect annual herbs, 10–60 cm tall; main stem simple or branched, terrete smooth or scabridulous in younger parts. Cataphylls, stipules 1.5–1.9 mm long, deltoid acuminate blade 1–1.5 mm long, subulate acuminate. Deciducus branchlets 1.5–14 cms long, subserete, smooth or a few lower nodes sometimes scabridulcus with 13–30 distichous leaves. Leaves 3–11×1.5×6 mm elliptic oblong obovate, oblong, or even obovate, obtuse, or minutely apiculate at apex, obtuse or slightly inequilateral at base, petioles 0.3–0.5 mm long, stipules 0.8–1.1 mm long triangular accuminate. Flowers in axillary, unsexual and bisexual cymles on deciduous branches. Proximal 2–3 axis with unisexual cymules, each consisting of 1 male and 1 female or 2(−3) males and female or 1 male and 2 female flower or combination thereof; male flowers pedicals at anthesis ca 1 mm long. Calyx lobe 5, subequal each ca 0.7×0.3 mm elliptic or oblong elliptic and abruptly acute at apex hyaline with unbranched mid ribs. Disc segments 5, roundish stames 3 (rarely 2): filaments connate into a column 0.2–0.3 mm high autheros sessile a top dehiscing longitudinally. Female flowers; pedicles 0.8–1 mm long, obtusely 4 gonous, dialated above, ca 1.5 mm in fruits, calyx 5 lobes, subequal. Ovate-oblong, acute at apex, midsepaline band green. Disc flat, deeply 5 lobes. Lobes sometimes toothed at apex. Styles 3, free, more or less spreading, shallowly bifid at apex; arms divergent (Mitra & Jain, Bull Bot Surv Ind 1985;27:167–176).

Historical Use of *P. Niruri* in Jaundice

Even though clinical uses of *P. niruri* and other species vz. *P. amarus* cited for over a century in the Ayurvedha and Siddha literatures, scientific evaluatory studies have been attempted only during the last 50 years for its efficacy in the treatment of jaundice/viral hepatitis. A logical approach towards identification of the active principles of *P. amarus* is to fractionate the plant extracts and identify biologically active compounds and to chemically characterise them.

Studies on *P. Niruri/P. Amarus* Against HBV

The first ever designed invitro antiviral study on *Phyllanthus niruri* against any hepatitis virus with HBV as model was reported by Thyagarajan in 1979 from Madras (Thyagarajan, Ph.D. Thesis, University of Madras 1979), India. Subsequently, Thyagarajan et al (1982) have shown the whole plant extract of *P. niruri* through several solvents brought about binding of Hepatitis B surface antigen (HBsAg) (Thygarajan et al., Ind J Med Res 1982; 76(Suppl.): 124–130. This plant from Tamilnadu, India was later identified taxonomically by Unander as *P. amarus*. Venkateswaran et al (1987) (Proc Natl Acad Sci USA 1989;14:195–201) and Blumberg et al (1989) (Cancer detection and prevention 1987;84:274–278). from United States using the *P. amarus* plants provided by Thyagarajan have shown that the plants collected from Madras, India whose aqueous extracts bound the surface antigen of HBV invitro, have inhibited the viral DNA polymerase (DNAp) of HBV and Woodchuck hepatitis virus (WHV) invitro. When administered intraperitoneally to WHV infected woodchucks, acutely infected animals lost the viral surface antigen; the surface antigen titre dropped in some chronically infected animals; the liver cancer rat in treated chronically infected animals was lower than the untreated controls.

Based on these findings they had secured an Australian patent numbered AV-A-56530/86 for a composition of matter useful in the treatment of Hepatitis B virus infection consisting essentially of the methanol extractable components of *P. niruri* L.

Yanagi et al., (Meeting on Hepatis viruses, Sep. 25–28, 1989, Cold Spring Haror Laboratory, NY, 1989,77) from Japan have reported at aqueous extracts of high dilutions of *P. amarus* collected from South India inhibited HBV DNAp, DNApI, T4-DNAp, the Klenow fragment and reverse transciptase of avian myeloblastosis virus. Shead et al (1990) (1990 International symposium on viral Hepatitis and liver diseases, Apr. 4–8, 1990, Houston, Tex., USA; A602) from Australia have s the aqueous extracts to inhibit the endogenous DNAp of DHBV at high dilutions. Niu etal (1990) form Australia in collaboration with Thyagarajan from India using *P. amarus* collected from Madras, Tamilnadu, on of 4–5 week old ducks congenitally infected with Duck hepatitis B virus (DHBV) with suitable controls after a period of 10 weeks treatment showed transient reduction of viral DNA in serum but no effect on the level of virus DNA or surface antigen in the liver (J Med Virol 1990;32:212–218).

Jayaram et al (1996) (Ind J Pathol Microbiol 1996;39(3) :211–215) reported invitro inhibition of HBsAg secretion by PLC/PRF/5 (Alexander) cellline for 48 hrs when the cellline was treated with 1 mg/ml concentration of *P. amarus* as a single dose. Lee et al (1996) (European J Clin Invest 1996; 26:1069–76) from USA in collaboration with Thyagarajan have shown that *P. amarus* down-regulates Hepatitis B virus m RNA transcription and replication using transgenic mice and transgenic celllines. The continuation of this collaboration by Ott et al (1997) has shown the cellular and molecular mechanism of HBV suppression by *P. amarus* to be by interrupting interactions between HBV enhancer I and cellular transcription factors (European 3 Clin Invest 1997; 27:908–915).

The biosafety studies on *P. amarus* dates back to 1971 when Mokkshasmit et al from Thailand using *P. niruri* have reported it to be non toxic to mice at 10 gms/kg body weight (Bull of Dept of Medical Science NAPRALERT Chicago, Ill., 1971;12:36–65). Rao (1985) from Andhra Pradesh, India reported 20% aqueous extct of *P. niruri* leaves to be effective to be as an oral pretreatment of 0.2 ml/100 mg body weight against $CCl_4$ induced hepatotoxicity in rats (Probe 1985;115–119). Syamasundar et al (1985) from Uttar Pradesh, India showed the hexane extracted compounds Phyllanthin and Hypo phyllanthin reduced $CCl_4$ or galatosamine induced cytotoxicity to cultured rat hepatocytes (J Ethnopharmacol 1985;14:41–44). Jayaram et al (1987) from Madras, India using the aqueous extract of dried whole plant showed no chronic toxicity in mice at 0.2 mg daily dose per animal for 90 days as revealed by physiological, biochemical and histopathological parameters. There was also no cytotonic or cytotoxic changes when tested in a tissue culture model using vero cell line (Biomedicine 1987;7:9–16). Venkateswaran et al (1987) from USA demonstrated its invivo safety using woodchucks as animal models, while Niu et al (1990) from Australia have shown *P. amarus* to be non toxic in Pekin ducks chronically infected with duck Hepatitis B virus. Jayaram and Thyagarajan (1994) studying the effect of *P. amarus* on β-galactosamine induced hepatoxicity on isolated rat hepatocytes have shown that a) *P. amarus* by itself did not bring about any hepatotoxicity on rat hepatocytes. b) At 1 mg/ml concentration the aqueous extract were shown to protect isolated rat hepatocytes significantly from β-galactosamine induced hepatoxicity thus proving the anti hepatoxicity potentials of *P. amarus* (Ind J Med Microbiol 1994;12(4) :247–250).

In all the traditional medicine systems, there has been several formulatory medicines for the treatment of jaundice in general without taking into consideration their viral etiology. Even though *P. niruri* was one of the constituents of such medicines, these were always been multiherbal preparations containing anywhere upto 12 medicinal herbs and most of the treatment evaluations were based on clinical improvement only. On the other hand, there is no documented trial report on their use in chronic liver disease patients.

It was in this context Thyagarajan and his collaborators, after proving the invitro and invivo efficacy and safety of *P. amarus* conducted 2 open clinical trials in acute viral hepatitis cases and seven clinical trials (2 of them being double blind trials and the others Phase I/II open trials) in chronic carriers of Hepatitis B virus (HBV). Jayanthi et al (1988) ( Gastroenterol and Hepatol 1988; 3:533–534) in a control clinical trial in acute viral hepatitis (AVH) using *P. niruri* on one arm, and other herbal medicines in other groups have shown a significantly greater decrease in transaminases after two weeks treatment with *P. niruri* in both HBsAg positive and negative groups. In a virologically characterised AVH clinical trial, Geetha et al (1992) (J Gen Medicine 1992;4(2):53–58) have shown that a) *P. amarus* treatment has brought about significantly faster biochemical normalcy in both hepatitis A and B; b) there was a higher rate of HBsAg clearance in *P. amarus* treated AVH-B cases than other treatment modalities and c) there was no observable side effects due to *P. amarus* treatment.

The clinical trials were conducted by Thyagarajan et al between 1988 and 1997. While the first trial 1988 (Lancet 1988; 2:764–766) reported 59% HBsAg clearance in the *P. amarus* treated group, as against 4% in the placebo group, the second open trial (1990) (Lancet 1990;2: 949–950) showed 20% HBsAg clearance and 63.6% loss of infectivity indicated by HBeAg sero-conversion. Parallely, investigators from other countries like Leeiarasamee et al (1990) (Lancet 1990;1:1600–1601) from Thailand, Wang Me Xia et al from China (1991) (Hepatology RLR 1991;21(5):22–24) have reported the non reproducibility of treatment efficacy by the local variety of *P. amarus* grown in their respective countries.

DISCLOSURE OF THE INVENTION

Concept & Hypothesis

Figure 1:
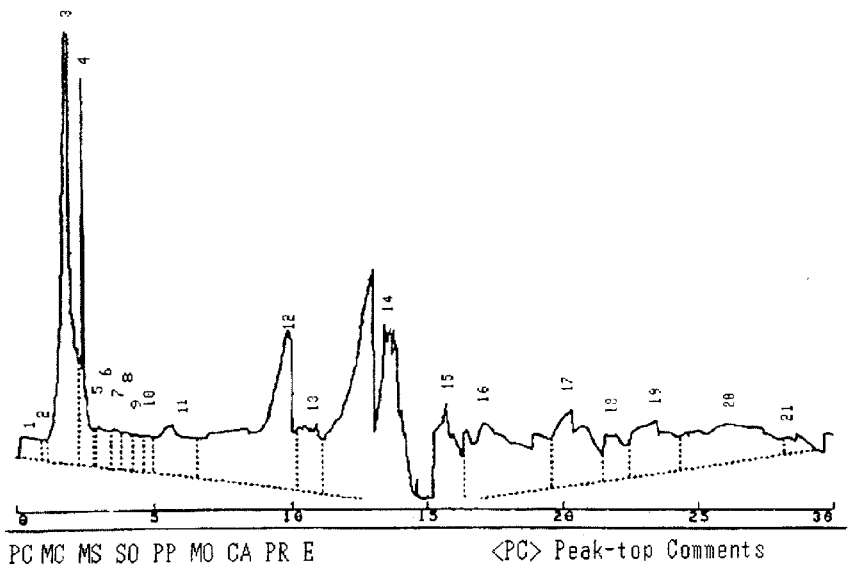
FIG. 1 depicts the HPLC pattern of the formulation that was prepared by the process that is described in Example 1.

It was the feeling that the non-reproducibility of treatment efficacy of the extract of the plant *Phyllanthus amarus* was due to the absence in the extract of all the under mentioned antiviral and biological properties which are essentially required for the efficient treatment of Hepatitis B (both acute and chronic) Hepatitis C (both acute and chronic) and other related viral infections of the liver.

(i) HBsAg binding property facilitating the inactivation of the virus in circulation ultimately leading to viral clearance (ii) HBV-DNA polymerase enzyme inhibiting potential, thus acting as anti-viral preventing the multiplication of HBV.

(iii) Reverse Transcriptase enzyme inhibition also required for the initiation of HBV replication.

(iv) inhibition of HBsAg secretion from HBV transinfected liver cells thus possessing activity against virus infected chronic liver disease conditions.

(v) Hepatoprotective and antihepatotoxic properties against the liver cell toxicity brought about by all hepatits viruses (A,B,C,D & E) and other hepatotoxic agents.

(vi) Immunomodulating property to potentiate the immune system of HBV infected patients towards virus clearance and protective antibody (anti HBs) responses.

(vii) HCV replication inhibition as shown by converting HCV-RNA positivity to HCV-RNA negativity thus possessing activity against HCV infected chronic liver disease conditions.

In the light of the above mentioned studies coupled with the above mentioned observations, it was necessary to explain the reasons for non-reproducibility of the clinical efficacy of *P. amarus* on one hand and to conduct further clinical trials independently in different places using the *P. amarus* preparation of Thyagarajan. Accordingly clinical trials were conducted on a total of 173 chronic HBV carriers (3 in Chennai (Madras), 1 at Vellore and 1 at Glasgow, UK) subsequent to the earlier to published clinical trials on 98 chronic HBV carriers. The result are presented in Table 3.

TABLE 3

Summary of seven clinical trials conducted by Thyagarajan and his collaborators on Human HBV carriers using P. amarus grown in Tamilnadu - For convenience it is termed as "University preparation."

| Clinical Trial | | Dosage/ Mgms/ | | Number treated | | HbsAg clearance % | | HbsAg sero-conversion % | |
|---|---|---|---|---|---|---|---|---|---|
| No. | Authors/year | tds | Duration | Test | Placebo | Test | Placebo | Test | Placebo |
| 1. | Published Thyagarajan et al (1988) | 200 | 1 m | 40 | 38 | 59 | 4 | ND | ND |
| 2. | Madras Thyagarajan et al (1990) Madras | 250 | 3 m | 20 | Nil | 20 | — | 63.6 | — |

TABLE 3-continued

Summary of seven clinical trials conducted by
Thyagarajan and his collaborators on
Human HBV carriers using P. amarus grown in Tamilnadu -
For convenience it is termed as "University preparation."

| Clinical Trial No. | Authors/year | Dosage/ Mgms/ tds | Duration | Number treated Test | Number treated Placebo | HbsAg clearance % Test | HbsAg clearance % Placebo | HbsAg sero-conversion % Test | HbsAg sero-conversion % Placebo |
|---|---|---|---|---|---|---|---|---|---|
| 3. | Unpublished Benjamin Samuel et al (1991), Vellore | 250 | 2 m | 10 | 12 | 20 | 8.3 | 37.5 | 0 |
| 4. | Thyagarajan et al (1992), Madras | 250 | 6 m | 72 | Nil | 25 | — | 54.0 | — |
| 5. | Thyagarajan et al (1993), Madras | 500 | 3 m | 8 | 8 | 25 | 0 | 71.4 | 16.0 |
| 6. | Eric Walker et al (1993–95) Glasgow | 500 | 4–6 m | 26 | Nil | 11.6 | — | 45.4 | — |
| 7. | Thyagarajan et al (1996–97), Madras | 500 | 6 m | 37 | Nil | 18.9 | — | 60.0 | — |
| | Total | | | 213 | 58 | 25.6 | 3.4 | 55.3 | 1.7 |

ND - Not done

In summary, these trials have shown a mean HBsAg clearance rate of 25.6% and mean HBeAg seroconversion rate of 55.3%. It was finally decided to recommend a schedule of 500 mg dosage of *P. amarus* preparation in capsules given orally for three times daily for six months.

*Phyllanthus amarus* Treatment in Acute and Chronic Hepatitis C

Available literature in the public domain did not reveal any report on the use of *Phyllanthus amarus* in the treatment of acute and chronic hepatitis C virus infection which is another major liver pathogen leading to significant morbidity and mortality. Hence the formulation of *Phyllanthus amarus* envisaged by the present invention was utilised to conduct two clinical trials to treat acute and chronic hepatitis C. Confidential clinical trials have been conducted using the formulation of *Phyllanthus amarus* in the form of capsules provided by Thyagarajan et al from Chennai. Results are presented in Table 4 and 6.

Since there are no experimental animal/tissue culture models available for testing specific antiviral properties against Hepatitis C virus (HCV), direct studies on human volunteer infected with HCV were conducted. Ethical clearance and informed consents from the study participants were obtained based on the high safety profile of the preparation of *P. amarus* prepared by the applicants as described above. Table.4. First Set of Case Studies on the Efficacy of the Preparation of *Phyllanthus amarus* Treatment on Chronic Hepatitis C Infections Conducted at Glasgow, UK(Eric Walker et al)

1. Patient Having the Date of Birth 07/02/49
Summary: The major finding has been the marked improvement in symptoms when the patient was treated with the preparation of *Phyllanthus amarus* which symptoms relapsed on 2 occasions when the treatment was withdrawn. The liver enzymes deteriorated when the preparation of *Phyllanthus amarus* was withdrawn and improved when it was started again. The patient has always been PCR positive. Appearance is of someone who is getting a 'liver protective effect' but without elimination of virus. Source was blood transfusion.

29/01/96—Liver biopsy—some inflammation and hepatic fibrosis consistent with chronic hepatitis C infection. Itch, joint pains, lethargy were the main symptoms. Not keen on interferon—Treatment with the preparation of *Phyllanthus amarus* was started 23/04/96—The weight of the patient increased by 2 kgs. Markedly improved energy and symptoms. Little change in liver enzymes (AST 42,ALT 50). PCR positive 15/05/96 treatment with the preparation of the composition containing *Phyllanthus amarus* was stopped 17/06/96—Itch, joint pains and lethargy returned (AST 46, ALT 50)

11107/96—Treatment with the composition containing *phyllanthus amaraus* was restarted 10/09/96—Symptoms were much improved (AST 46, ALT 71)

01/07/97—Still hepatitis C PCR positive(genotype 3). Repeat liver biopsy shows little change (inflammation and fibrosis but no active cirrhotic changes)

05/06/98—weight of the patient was found to be steady and the patient felt well (AST 42, ALT 59)

08/08/98—Treatment with the preparation of *Phyllanthus amarus* was stopped

31/12198—The patient was found to be depressed and 'run down'(AST 62, ALT 75)

211011/99—Treatment with the preparation of Phyllanthus restarted following which a marked improvement in the patient's feeling of well being was observed.

29/12/99—The patient felt well (AST 50, ALT 69), remained PCR positive

2. Patient Having a Date of Birth 20/06/54
Source of HCV infection was intravenous drug use
This patient was one of the first to clear HBsAg and 'e' antigen after treatment with the preparation of Phyllanthus tamarus back in 1990—he remains negative (1999) He was not tested for hepatitis C until 1999 (April) when he was found to have antibody but was PCR positive. He remained well.

A second set of studies have been carried out by the inventor. Results confirming the efficacy of the new formulation for the treatment of acute and chronic Hepatitis B & C and other related infections of liver are summarised in Table—6.

THE INVENTION

We observed that if all the above said six essential properties are made available in a single formulation, the resulting formulation will have uniform and stable antiviral and biological potentials which will be beneficial and optimal for the treatment of acute and chronic hepatitis B & C and other viral diseases of the liver. Based on the above findings, the R & D work for the development of a new formulation of *P. amarus* extract was initiated to find out which formulation will be active significantly against both acute Hepatitis B and against chronic HBV carriers. Accordingly, R & D was directed towards developing such a formulation from the plant *Phyllanthus amarus* containing all the above said essential characteristics which have not only efficient clinical and biological efficacy against acute and chronic Hepatitis B; acute and chronic Hepatitis C and other viral infections of the liver but also have uniform and stable antiviral and bio active properties.

OBJECTIVES OF THE INVENTION

Accordingly, the main objective of the present invention, therefore, is to provide a pharmaceutical formulation having uniform and stable antiviral and biological efficacy which is useful for the treatment of acute and chronic Hepatitis B. Hepatitis C, chronic HIV carriers and other related viral infections of the liver from the plant, *Phyllanthus amarus*

Another objective of the present invention is to provide a pharmaceutical formulation useful for the treatment of Hepatitis B, Hepatitis C , chronic HIV carriers and other related viral infections of the liver from the plant *Phyllanthus amarus* which brings about binding of Hepatitis B surface antigen (HBsAg) of the Hepatitis B virus, thus facilitating the inactivation of the virus in circulation ultimately leading to viral clearance.

Yet another objective of the present invention is to provide a pharmaceutical formulation useful for the treatment of Hepatitis B, Hepatitis C, chronic HIV carriers and other related viral infections of the liver from the plant *P. amarus* which inhibit the HBV-DNA polymerase enzyme required for the replication for the virus, thus acting as antiviral preventing the multiplication of the virus itself.

Still another objective of the present invention is to provide a pharmaceutical formulation useful for the treatment of Hepatitis B, Hepatitis C, chronic HIV carriers and other related viral infections of the liver from the plant *P. amarus* which inhibits the Reverse Transcriptase enzyme which is also required for the initiation of HBV replication and is the chief enzyme required for the replication of the AIDS virus, Human Immunodeficiency virus (HIV).

Another objective of the present invention is to provide a process for the preparation of a pharmaceutical formulation useful for the treatment of Hepatitis B, Hepatitis C, chronic HIV carriers and other related viral infections of the liver from the plant *P. amarus* which is hepatoprotective and also possess antihepatotoxic properties against the liver cell toxicity brought about by all Hepatitis viruses (A,B,C,D & E) and other hepatotoxic agents including chemicals and aflatoxins.

Yet another objective of the present invention is to provide a pharmaceutical formulation useful for the treatment of acute and chronic Hepatitis B; acute and chronic Hepatitis C, chronic HIV carriers and other related viral infections of the liver from the plant *P. amarus* which is anti-inflammatory and also possesses the property of normalising the transaminase enzymes level indicating antihepatotoxic and liver cell regenerating potentials of the formulation.

Still another objective of the present invention is to provide a pharmaceutical formulation useful for the treatment of acute and chronic Hepatitis B; acute and chronic Hepatitis C , chronic HIV carriers and other related viral infections of the liver from plant *P.amarus* which inhibited the Hepatitis C virus replication as revealed by conversion from HCV-RNA positivity to HCV-RNA negatitvity in patients treated by the formulation.

Another objective of the present invention is to provide a pharmaceutical formulation useful for the treatment of acute and chronic Hepatitis B; acute and chronic Hepatitis C, chronic HIV carriers and other related viral infections of the liver from plant *P.amarus* which is immunomodulatory as revealed by increased T-cell proliferation.

Still another objective of the present invention is to provide a pharmaceutical formulation useful for the treatment of acute and chronic Hepatitis B, acute and chronic Hepatitis C and other related viral infections of the liver from the plant *P. amarus* in which the antiviral and biological activities are uniform.

Yet another objective of the present invention is to provide a process for the preparation of a pharmaceutical formulation useful for the treatment of acute and chronic Hepatitis B acute and chronic Hepatitis C and other related viral infections of the liver from the plant *P. amarus* with antihepatotoxic, liver cell regenerating and immunomodulating potentials.

The invention is based on our surprising findings that when the parts of the plant *Phyllanthus amarus* are extracted separately with a polar solvent alone, mixture of polar solvent and water and water alone and when the extracts so obtained are mixed together, the resultant formulation is found to have all the under mentioned properties which are required for the efficient treatment of Hepatitis B (both acute and chronic), Hepatitis C (both acute and chronic) and other related viral infections of the liver.

(i) HBsAg binding property facilitating the inactivation of the virus in circulation ultimately leading to viral clearance.

(ii) HBV-DNA polymerase enzyme inhibiting potential, thus acting as anti-viral, preventing the multiplication of HBV.

(iii) Reverse Transcriptase enzyme inhibition also required for the initiation of HBV replication.

(iv) Inhibition of HBsAg secretion from HBV transinfected liver cells thus possessing activity against virus infected chronic liver disease conditions.

(v) Hepato-protective, anti-inflammatory, antihepatotoxic and liver cell regenerative properties against the liver cell toxicity brought about by all hepatitis viruses (A,BC,D & E) and other hepatotoxic agents.

(vi) Immunomodulating property to potentiate the immune system of HBV infected patients towards virus clearance and protective antibody (anti HBs) responses.

(vii) HCV-replication inhibition as shown by converting HCV-RNA positivity to HCV-RNA negativity thus possessing activity against HCV infected chronic liver disease conditions.

It is observed that the individual extracts of the plant *Phyllanthus amarus* namely the extract obtained by using a polar solvent alone, extract obtained by using a polar solvent and water and the extract obtained by using water alone, themselves, does not possess all the above said essential characteristics. But the combination of the above mentioned extracts imparts to the resulting formulation all the above mentioned essential properties which are required for the efficient treatment of Hepatitis B (both acute and chronic), Hepatitis C (both acute and chronic) and other related viral infections of the liver. These properties are acquired by the formulation due to the biological synergism of the different components contained in the individual extracts when combined to form the formulation.

The pharmaceutical formulation of the present invention is not, therefore, a mere admixture of the individual components resulting in the aggregation of the properties of the individual components but is a novel pharmaceutical formulation having biological synergism of all the required efficacious antiviral and biological properties of the components employed.

Accordingly, the present invention provides a pharmaceutical formulation useful for the treatment of Hepatitis B (both acute and chronic) Hepatitis C (both acute and chronic) and other related viral infections of the liver which comprises (i) an extract of the plant *Phyllanthus amarus* obtained by using a polar solvent alone (ii) an extract of the plant *Phyllanthus amarus* obtained by using a mixture of a polar solvent and water and (iii) an extract of the plant *Phyllanthus amarus* obtained by using water alone According to another feature, the present invention provides a pharmaceutical formulation useful for the treatment of Hepatitis B (both acute and chronic), Hepatitis C (both acute and chronic) and other related viral infections of the liver which comprises (i) 10 to 40% w/w of an extract of the plant *Phyllanthus amarus* obtained by using a polar solvent alone (ii) 10 to 40% w/w of an extract of the plant *Phyllanthus amarus* obtained by using a mixture of a polar solvent and water wherein the ratio of the solvent to water ranges from 20 to 80 and 80 to 20% w/w respectively and (iii) 10 to 40% w/w of an extract of the plant *Phyllanthus amarus* obtained by using water alone In another preferred embodiment of the invention, there is provided a pharmaceutical formulation useful for the treatment of Hepatitis B (both acute and chronic), Hepatitis C (both acute and chronic) and other related viral infections of the liver which comprises (i) 20 to 30% w/w of an extract of the plant *Phyllanthus amarus* obtained by using a polar solvent alone (ii) 20 to 40% w/w of an extract of the plant *Phyllanthus amarus* obtained by using a mixture of a polar solvent and water wherein the ratio of the solvent to water ranges from 80 to 20% and 20 to 80% w/w respectively (iii) 20 to 40-% w/w of an extract of the plant *Phyllanthus amarus* obtained by using a polar solvent and water wherein the solvent to water ratio ranges from 20 to 80% and 80 to 20% w/w respectively and (iv) 20 to 30% w/w of an extract of the plant *Phyllanthus amarus* obtained by using water alone In still another preferred embodiment of the present invention there is provided a pharmaceutical formulation useful for the treatment of Hepatitis B (both acute and chronic), Hepatitis C (both acute and chronic) and other related viral infections of the liver which comprises one part each of an extract of the plant *Phyllanthus amarus* obtained by using a polar solvent alone, an extract of the plant *Phyllanthus amarus* obtained by using a mixture of a polar solvent and water and an extract of the plant *Phyllanthus amarus* using water alone.

In yet another preferred embodiment of the present invention, there is provided a pharmaceutical formulation useful for the treatment of Hepatitis B (both acute and chronic), Hepatitis C (bath acute and chronic) and other related viral infections of the liver which comprises one part each of (i) 10 to 40% w/w of an extract of the plant *Phyllanthus amarus* obtained by using a polar solvent alone.

(ii) 10 to 40% w/w of an extract of the plant *Phyllanthus amarus* obtained by using a mixture of a polar solvent and water wherein the ratio of the solvent to water ranges from 20 to 80 and 80 to 20% w/w respectively and (iii) 10 to 40% w/w of an extract of the plant *Phyllanthus amarus* obtained by using water alone.

In another prefrred embodiment of the present invention, there is provided a pharmaceutical formulation useful for the treatment of Hepatitis B (both acute and chronic), Hepatitis C (both acute and chronic) and other related viral infections of the liver which comprises one part each of (i) 20 to 30% w/w of an extract of the plant *Phyllanthus amarus* obtained by using a polar solvent alone, (ii) 20 to 40% w/w of an extract of the plant *Phyllanthus amarus* obtained by using a mixture of a polar solvent and water wherein the ratio of the solvent to water ranges from 80 to 20% and 20 to 80% w/w respectively (iii) 20 to 40% w/w of an extract of the plant *Phyllanthus amarus* using a mixture of a polar solvent and water wherein the ratio of the solvent to water ranges from 20 to 80% w/w and 80 to 20% w/w respectively and (iv) 20 to 30% w/w of an extract obtained using water alone In still another preferred embodiment of the present invention, there is provided a pharmaceutical formulation useful for the treatment of Hepatitis B (both acute and chronic), Hepatitis C (both acute and chronic) and other related viral infections of the liver which comprises two parts (i) of an extract of the plant *Phyllanthus amarus* obtained by using a polar solvent alone and one part each of (ii) of an extract of the plant *Phyllanthus amarus* obtained by using a mixture of a polar solvent and water and (iii) an extract of the plant *Phyllanthus amarus* using water alone In yet another preferred embodiment of the present invention, there is provided a pharmaceutical formulation useful for the treatment of Hepatitis B (both acute and chronic), Hepatitis C (both acute and chronic) and other viral infections of the liver which comprises two parts (i) of 10 to 40% w/w of an extract of the plant *Phyllanthus amarus* obtained by using a polar solvent and one part each (ii) of 10 to 40% w/w of an extract of the plant *Phyllanthus amarus* obtained by using a mixture of a polar solvent and water wherein the ratio of the solvent to water ranges from 20 to 80% and 80 to 20% w/w respectively (iii) of 10 to 40% w/w of an extract of the plant *Phyllanthus amarus* obtained by using water alone In yet another preferred embodiment of the present invention there is provided a pharmaceutical formulation useful for the treatment of Hepatitis B (both acute and chronic), Hepatitis C (both acute and chronic) and other viral infections of the liver which comprises two parts
- (i) of 20 to 30% W/W of an extract of the plant *Phyllanthus amarus* obtained by using a polar solvent alone and one part each
- (ii) of 20 to 40% w/w of an extract of the plant *Phyllanthus amarus* obtained by using a mixture of a polar solvent and water wherein the ratio of the solvent to water ranges from 80 to 20% and 20 to 80% w/w respectively
- (iii) of 20 to 40% w/w of an extract of the plant *Phyllanthus amarus* obtained by using a mixture of polar solvent and water wherein the ratio of the solvent to water ranges from 20 to 80% w/w and 80 to 20% w/w respectively and
- (iv) of 20 to 30% w/w of an extract of the plant *Phyllanthus amarus* obtained by using water alone.

In yet another preferred embodiment of the invention, there is provided a process for the preparation of pharmaceutical formulation useful for the treatment of Hepatitis B (acute and chronic), Hepatitis C (both acute and chronic) and other related viral infections of the liver which comprises mixing
- (i) an extract of the plant *Phyllanthus amarus* obtained by using a polar solvent alone
- (ii) an extract of the plant *Phyllanthus amarus* obtained by using a mixture of a polar solvent and water and
- (iii) an extract of the plant *Phyllanthus amarus* obtained by using water alone According to another feature the present invention, provides a process for preparing a pharmaceutical formulation useful for the treatment of Hepatitis B (both acute and chronic), Hepatitis C (both acute and chronic) and other related viral infections of the liver which comprises mixing
- (i) 10 to 40% w/w of an extract of the plant *Phyllanthus amarus* obtained by using a polar solvent alone
- (ii) 10 to 40% w/w of an extract of the plant *Phyllanthus amarus* obtained by using a mixture of a polar solvent and water wherein the ratio of the solvent to water ranges from 20 to 80 and 80 to 20% w/w respectively and
- (iii) 10 to 40% w/w of an extract of the plant *Phyllanthus amarus* obtained by using water alone In another preferred embodiment of the invention, there is provided a process for the preparation of a pharmaceutical formulation useful for the treatment of Hepatitis B (both acute and chronic), Hepatitis C (both acute and chronic) and other related viral infections of the liver which comprises mixing
- (i) 20 to 30% w/w of an extract of the plant *Phyllanthus amarus* obtained by using a polar solvent alone
- (ii) 20 to 40% w/w of an extract of the plant *Phyllanthus amarus* obtained by using a mixture of a polar solvent and water wherein the ratio of the solvent to water ranges from 80 to 20% and 20 to 80% w/w respectively
- (iii) 20 to 40-% w/w of an extract of the plant *Phyllanthus amarus* obtained by using a polar solvent and water wherein the solvent to water ratio ranges from 20 to 80% and 80 to 20% w/w respectively and
- (iv) 20 to 30% w/w of an extract of the plant *Phyllanthus amarus* obtained by using water alone In still another preferred embodiment of the present invention, there is provided a process for the preparation of pharmaceutical formulation useful for the treatment of Hepatitis B (both acute and chronic), Hepatitis C (both acute and chronic) and other related viral infections of the liver comprises mixing one part each of
- (i) an extract of the plant *Phyllanthus amarus* obtained by using a polar solvent alone,
- (ii) an extract of the plant *Phyllanthus amarus* obtained by using a mixture of a polar solvent and water and
- (iii) an extract of the plant *Phyllanthus amarus* using water alone In yet another preferred embodiment of the present invention, there is provided a process for the preparation of pharmaceutical formulation useful for the treatment of Hepatitis B (both acute and chronic), Hepatitis C (both acute and chronic) and other related viral infections of the liver which comprises mixing one part each of
- (i) 10 to 40% w/w of an extract of the plant *Phyllanthus amarus* obtained by using a polar solvent alone.
- (ii) 10 to 40% w/w of an extract of the plant *Phyllanthus amarus* obtained by using a mixture of a polar solvent and water wherein the ratio of the solvent to water ranges from 20 to 80 and 80 to 20% w/w respectively and
- (iii) 10 to 40% w/w of an extract of the plant *Phyllanthus amarus* obtained by using water alone In another preferred embodiment of the present invention there is provided a process for the preparation of a pharmaceutical formulation useful for the treatment of Hepatitis B (both acute and chronic), Hepatitis C (both acute and chronic) and other related viral infections of the liver which comprises mixing one part each of
- (i) 20 to 30% w/w of an extract of the plant *Phyllanthus amarus* obtained by using a polar solvent alone,
- (ii) 20 to 40% w/w of an extract of the plant *Phyllanthus amarus* obtained by using a mixture of a polar solvent and water wherein the ratio of the solvent to water ranges from 80 to 20% and 20 to 80% w/w respectively
- (iii) 20 to 40% w/w of an extract of the plant *Phyllanthus amarus* using a mixture of a polar solvent and water wherein the ratio of the solvent to water ranges from 20 to 80% w/w and 80 to 20% w/w respectively and
- (iv) 20 to 30% w/w of an extract obtained using water alone In still another preferred embodiment of the present invention, there is provided a process for the preparation of a pharmaceutical formulation useful for the treatment of Hepatitis B (both acute and chronic), Hepatitis C (both acute and chronic) and other related viral infections of the liver which comprises mixing two parts
- (i) of an extract of the plant *Phyllanthus amarus* obtained by using a polar solvent alone and one part each of
- (ii) of an extract of the plant *Phyllanthus amarus* obtained by using a mixture of a polar solvent and water and
- (iii) an extract of the plant *Phyllanthus amarus* using water alone In yet another preferred embodiment of the present invention, there is provided a process for the preparation of a pharmaceutical formulation useful for the treatment of Hepatitis B (both acute and chronic), Hepatitis C (both acute and chronic) and other viral infections of the liver which comprises mixing two parts
- (i) of 10 to 40% w/w of an extract of the plant *Phyllanthus amarus* obtained by using a polar solvent and one part each
- (ii) of 10 to 40% w/w of an extract of the plant *Phyllanthus amarus* obtained by using a mixture of a polar solvent and water wherein the ratio of the solvent to water ranges from 20 to 80% and 80 to 20% w/w respectively (iii) of 10 to 40% w/w of an extract of the plant *Phyllanthus amarus* obtained by using water alone In yet another preferred embodiment of the present invention, there is provided a process for the preparation pharmaceutical formulation useful for the treatment of Hepatitis B (both acute and chronic), Hepatitis C (both acute and chronic) and other viral infections of the liver which comprises mixing two parts (i) of 20 to 30% W/W of an extract of the plant *Phyllanthus amarus* obtained by using a polar solvent alone and one part each (ii) of 20 to 40% w/w of an extract of the plant *Phyllanthus amarus* obtained by using a mixture of a polar solvent and water wherein the ratio of the solvent to water ranges from 80 to 20% and 20 to 80% w/w respectively (iii) of 20 to 40% w/w of an extract of the plant *Phyllanthus amarus* obtained by using a mixture of polar solvent and water wherein the ratio of the solvent to water ranges from 20 to 80% w/w and 80 to 20% w/w respectively and (iv) of 20 to 30% w/w of an extract of the plant *Phyllanthus amarus* obtained by using water alone.

The present invention also envisages within its scope the use of the pharmaceutical composition of the present invention described above for the preparation of a medicament useful for treating Hepatitis B (both acute and chronic), Hepatitis C (both acute and chronic) and other related viral infections of the liver.

The invention further envisages the use of the pharmaceutical composition of the present invention in the treatment of Hepatitis B (both acute and chronic), Hepatitis C (both acute and chronic) and other related viral infections of the liver.

Furthermore the present invention also, within its scope includes, the use of the pharmaceutical composition described above for achieving antihepatotoxicity, liver cell regeneration and immunomodulation.

In another embodiment of the present invention there is provided a method of treating Hepatitis B (both acute and chronic), Hepatitis C (both acute and chronic) and other related viral infections of the liver which comprises administering a therapeutically effective dose of the pharmaceutical composition described above.

Extraction of the Components of the Formulation

Parts such as leaves, stems, seeds and roots of the taxonomically identified collections of the plant *Phyllanthus amarus* were dried and kept in an oven heated to a temperature in the range of 50 to 80 degree C. for a period in the range of 3 to 5 hrs a day. for a period of 3 to 6 successive days. The dried parts of the plants are then powdered. The powder thus obtained is used for the extraction of different components of the preparation of the formulation of the present invention.

Before subjecting the powder for extraction procedures, each batch of powder is subjected for sterility testing to rule out any bacterial or fungal contamination as per standard methods.

One portion of the powder is extracted with polar solvent. The polar solvent employed may be methanol, ethanol, hexane, butanol and the like. The extraction may be carried out at a temperature in the range of 37 to 60 degree C. for a period ranging from 2 hours to 18 hours preferably at a temperature in the range of 37 to 60 degree C. This extract may be used as the component (i) of the pharmaceutical formulation of the present invention.

Another portion of the powder is extracted with a mixture of polar solvent and water. The polar solvent employed may be methanol, ethanol, Hexane and the like. The ratio of the solvent and water used for extraction may range from 20 to 80 and 80 to 20% w/w respectively, The ratio may preferably range from 30 to 50% and 50 to 30% w/w respectively. The extraction may be carried out at a temperature in the range of 4 to 40 degree C. for 2 to 18 hours more preferably at a temperature in the range of 37 to 60 degree C. for 2 to 4 hours. This extract may be used as the component (ii) of the pharmaceutical formulation of the present invention.

Yet another portion of the powder is extracted with water alone. The extraction may be carried out at a temperature in the range of 37 to 60 degree C. for 2 to 18 hours. This extract may be used as the component (iii) of the pharmaceutical formulation of the invention The extracts so obtained may now be mixed together to obtain the pharmaceutical formulation of the present invention. The mixing may be effected in a vertex mixer or heating mantle and stirring it thoroughly till a homogenous formulation is obtained. The mixing may be effected at a temperature in the range of 37 to 60 degree C. for 15 to 30 minutes.

The details of the invention are given in the Examples provided below which are given to illustrate the invention only and therefore should not be construed to limit the scope of the present invention.

EXAMPLE 1

40 gms of the powder obtained as explained above is extracted with 200 ml of ethanol at a temperature of 35 to 37 degree C. for 2 hrs and 56 degree C. for another 2 hrs under shaking. Yield of the extract is 90 ml (EXTRACT-I)

40 gms of the powder obtained as explained above is extracted with a mixture of 160 ml of ethanol and 40 ml water total volume being 200 ml. The extraction was effected at a temperature of 35 to 37 degree C. for 2 hrs and 56–60 degree C. for another 2 hrs under shaking. Yield of the extract 65 ml (EXTRACT-II)

40 gms of the powder prepared as explained above is extracted with 200 ml water at temperature of 35 to 37 degree C. for 2 hrs and 56–60 degree C. for another 2 hrs under shaking. Yield of the extract 50 ml (EXTRACT-III)

Extracts I, II, and III were mixed in 1:1:1 ratio (i.e., 50 ml each) in a conical flask in an environmental shaker kept at 37° C. for 15–30 min. The resultant formulation was dried in a dessicator/"Verts" vaccum drier until the solvents get fully evaporated. The yield of the powdery formulation was 28 gms (20%).

EXAMPLE 2

40 gms of the powder obtained as explained above is extracted with 200 ml of ethanol at a temperature of 35 to 37 degree C. for 2 hrs and 56–60 degree C. for another 2 hrs under shaking. Yield of the extract 90 ml (EXTRACT-I)

40 gms of the powder obtained as explained above is extracted with a mixture of 160 ml of ethanol and 40 ml water total volume being 200 ml. The extraction was effected at a temperature of 35 to 37 degree C. for 2 hrs and 56–60 degree C. for another 2 hrs under shaking. Yield of the extract 65 ml (EXTRACT-II)

40 gms of the powder prepared as explained above is extracted with 200 ml water at temperature of 35 to 37 degree C. for 2 hrs and 56–60 degree C. for another 2 hrs under shaking. Yield of the extract 50 ml (EXTRACT-III)

The extracts I, II & III in 2:1:1 ratio (i.e., 80 ml of extract I: 40ml of extract II and 40 ml of extract III) were mixed in a conical flask in an environmental shaker kept at 37° C. for 15–30 min. The resultant formulation was dried in a dessicator/"Vertis" vaccum drier until the solvents get fully evaporated. The final yield when dried was 36 gms (25%).

EXAMPLE 3

30 gms of the powder obtained as explained above is extracted with 200 ml of methanol at a temperature of 35 to 37 degree C. for 2 hrs and 56–60 degree C. for another 2 hrs under shaking. Yield of the extract 90 ml (EXTRACT-I)

30 gms of the powder obtained as explained above are extracted with a mixture of 60 ml of methanol and 140 ml water. The extraction was effected at a temperature of 35 to 37 degree C. for 2 hrs and 56–60 degree C. for another 2 hrs under shaking. Yield of the extract 70 ml (EXTRACT-II)

30 gms of the powder prepared as explained above is extracted with 200 ml water at temperature of 35 to 37 degree C. for 2 hrs and 56–60 degree C. for another 2 hrs under shaking. Yield of the extract 50 ml (EXTRACT-III)

The Extracts I,II and III were mixed in 1:1:1 ratio (i.e., 50 ml each) in a conical flask in an environmental shaker kept at 37° C for 15–30 min. The resultant formulation was dried in a dessicator/"Vertis" vaccum drier until the solvents get fully evaporated. The yield of the powdery formulation was 25 gms (15%).

EXAMPLE 4

30 gms of the powder obtained as explained above is extracted with 200 ml of methanol at a temperature of 35 to 37 degree C. for 2 hrs and 56–60 degree C. for another 2 hrs under shaking. Yield of the extract 90 ml (EXTRACT-I)

30 gms of the powder obtained as explained above are extracted with a mixture of 60 ml of methanol and 140 ml water. The extraction was effected at a temperature of 35 to 37 degree C. for 2 hrs and 56–60 degree C. for another 2 hrs under shaking. Yield of the extract 70 ml (EXTRACT-II)

30 gms of the powder prepared as explained above is extracted with 200 ml water at temperature of 35 to 37 degree C. for 2 hrs and 56–60 degree C. for another 2 hrs under shaking. Yield of the extract 50 ml (EXTRACT-III)

The extracts I, II and III in 2:1:1 ratio (i.e., 80 ml of extract I: 40 ml of II and 40 ml of III) were mixed in a conical flask in an environmental shaker kept at 37° C. for 15–30 min. The resultant formulation was dried in a dessicator/"Vertis" vaccum drier until the solvents get fully evaporated. The final yield was 32 gms (22%).

EXAMPLE 5

40 gms of the powder obtained as explained above is extracted with 200 ml of methanol at a temperature of 56 to 60 degree C. for 4 hrs under shaking. Yield of the extract 90 ml 35 gms of the powder obtained as explained above is extracted with a mixture of 100 ml of methanol and 100 ml water, total volume being 200 ml. The extraction was effected at a temperature of 35 to 37 degree C. for 2 hrs and 56–60 degree C. for another 2 hrs under shaking. Yield of the extract 70 ml (EXTRACT-II)

30 gms of the powder prepared as explained above is extracted with 200 ml water at temperature of 56 to 60 degree C. for 4 hrs under shaking. Yield of the extract 60 ml (EXTRACT-III)

Extracts I, II and III were mixed in 1:1:1 ratio (i.e., 50 ml each) in a conical flask in an environmental shaker kept at 37° C. for 15–30 min. This formulation was dried in a dessicator/"Vertis" vaccum drier until the solvents get fully evaporated. The yield of the powdery formulation so obtained was 25 gms (15%).

EXAMPLE 6

40 gms of the powder obtained as explained above is extracted with 200 ml of methanol at a temperature of 56 to 60 degree C. for 4 hrs under shaking. Yield of the extract 90 ml (EXTRACT-I).

35 gms of the powder obtained as explained above is extracted with a mixture of 100 ml of methanol and 100 ml water, total volume being 200 ml. The extraction was effected at a temperature of 35 to 37 degree C. for 2 hrs and 56–60 degree C. for another 2 hrs under shaking. Yield of the extract 70 ml (EXTRACT-II)

30 gms of the powder prepared as explained above is extracted with 200 ml water at temperature of 56 to 60 degree C. for 4 hrs under shaking. Yield of the extract 60 ml (EXTRACT-III)

The Extracts I, II, III were mixed in 2:1:1 ratio (i.e., 80 ml of extract I: 40 ml of extract II and 40 ml of extract III) were mixed in a conical flask in an environmental shaker kept at 37° C. for 15–30 min. This formulation was dried in a dessicator/"Vertis" vaccum drier until the solvents get fully evaporated.The final yield when dried was 40 gms (25%).

EXAMPLE 7

40 gms of the powder obtained as explained above is extracted with 200 ml of methanol at a temperature of 35 to 37 degree C. for 2 hrs and 56–60 degree C. for another 2 hrs under shaking. Yield of the extract 90 ml (EXTRACT-I)

40 gms of the powder prepared as explained above is extracted with 200 ml water at a temperature of 35 to 37 degree C. for 2 hrs and 56–60 degree C. for another 2 hrs under shaking. Yield of the extract 60 ml (EXTRACT-II)

35 gms of the powder obtained as explained above is extracted with a mixture of 100 ml of methanol and 100 ml water, total volume being 200 ml. The extraction was effected at a temperature of 56 to 60 degree C. for 4 hrs under shaking. Yield of the extract 70 ml (EXTRACT-III)

30 gms of the powder obtained as explained above is extracted with a mixture of 60 ml of methanol and 140 ml water total volume being 200 ml. The extraction was effected at a temperature of 56 to 60 degree C. for 4 hrs shaking. Yield of the extract 65 ml (EXTRACT-IV)

The Extracts I, II, III and IV were mixed in 1:1:1:1 ratio (i.e., 50 ml each) in a conical flask in an environmental shaker kept at 37° C. for 15–30 min. The resultant formulation was dried in a dessicator/"Vertis" vaccum drier until the solvents get fully evaporated. The yield of the powdery formulations so obtained was 40 gms (25%).

EXAMPLE 8

40 gms of the powder obtained as explained above is extracted with 200 ml of methanol at a temperature of 35 to 37 degree C. for 2 hrs and 56–60 degree C. for another 2 hrs under shaking. Yield of the extract 90 ml (EXTRACT-I)

40 gms of the powder prepared as explained above is extracted with 200 ml water at a temperature of 35 to 37 degree C. for 2 hrs and 56–60 degree C. for another 2 hrs under shaking. Yield of the extract 60 ml (EXTRACT-II)

35 gms of the powder obtained as explained above is extracted with a mixture of 100 ml of methanol and 100 ml water, total volume being 200 ml. The extraction was effected at a temperature of 56 to 60 degree C. for 4 hrs under shaking. Yield of the extract 70 ml (EXTRACT-III)

30 gms of the powder obtained as explained above is extracted with a mixture of 60 ml of methanol and 140 ml water total volume being 200 ml. The extraction was effected at a temperature of 56 to 60 degree C. for 4 hrs shaking. Yield of the extract 65 ml (EXTRACT-IV)

The extracts I, II, III & IV were mixed in 2:1:1:1 ratio (i.e., 80 ml of extract I: 40 ml of extract II, 40 ml of extract III and 40 ml of extract IV) were mixed in a conical flask in an environmental shaker kept at 37° C. for 15–30 min. The resultant formulation was dried in a dessicator/"Vertis" vaccum drier until the solvents get fully evaporated. The final yield when dried was 48 gms (30%).

The examples given below are provided to compare the properties of the extract of the plant *Phyllanthus amarus* obtained using polar solvent alone and water alone with the properties of the pharmaceutical formulation of the present invention.

EXAMPLE 9

40 gms of the powder obtained as explained above is extracted with 200 ml of methanol at a temperature of 35 to 37 degree C. for 2 hrs and 56–60 degree C. for another 2 hrs under shaking. Yield of the extract 90 ml.

This extract as a formulation was dried in a dessicator/"Vertis" vacuum drier until the solvents get fully evaporated. The yield of the powdery formulations so obtained was 15 gms (12.5%).

EXAMPLE 10

40 gms of the powder prepared as explained above is extracted with 200 ml water at a temperature of 35 to 37 degree C. for 2 hrs and 56–60 degree C. for another 2 hrs under shaking. Yield of the extract 50 ml This extract was dried in a dessicator/"Vertis" vacuum drier until the water get fully evaporated. The yield of the powder so obtained was 8 gms (10%).

Biological Efficacy of the Pharmaceutical Formulation with Particular Reference to the Formulation Obtained by the Process Described in Examples 1 to 10

The powdery formulations obtained in the Examples 1 to 10 were used for the biological studies to confirm the presence of the above mentioned essential properties.

For these studies, Phosphate buffered saline (PBS) as vehicle in w/v concentration was employed.

The solutions of the formulations prepared as mentioned above were used for the following assay methods for confirming the presence of the essential properties mentioned above A. HBSAG Binding Property of the Pharmaceutical Formulation of the Invention Principle: The test is an enzyme immunoassay based on the sandwich principle. HBsAg in the plasma is neutralised or bound by pre-incubation with anti-HBs like substance, and hence no longer reacts with the antibody coated in the wells. The presence of HBsAg binding activity in the formulation of the present invention is demonstrated by reduction of colour or a negative ELISA result The presence of unbound HBsAg in a test sample is demonstrated by an increase in the colour or a positive ELISA result.

Procedure: Pre-incubation with HBsAg plasma: Equal volume of pre-titrated HBsAg positive plasma and 5 mg/ml concentration of the formulation of the present invention was mixed and incubated at 37° C. for 5 days. The mixture was assayed daily for the presence of bound/unbound HBsAg using Hepanostika (Organon) or any other commercial ELISA kit. Control tubes containing solvent (PBS) and plasma (solvent control) and *P. amarus* and plasma (positive control) were set up in each batch. ELISA was performed as per the instructions of the manufacturer given in the kit.

Calculation
1. Cutoff value: the cutoff value was calculated as mean negative control+0.025
2. Values equal to or greater than the cutoff should be taken as positive The results of the assays of the pharmaceutical formulation of the present invention prepared by the process described in the Examples 1 to 8 are given in Table 5.

B. HBV-DNA Polymerase Inhibiting Properties of the Pharmaceutical Formulation of the Invention Principle: Replication of Hepadna viruses involves a viral DNA polymerase which is a potential target for chemotherapy against HBV. In the presence of HBV-DNA polymerase, complementary bases are added to the template (HBV-DNA), the addition of which are quantitated with the help of tritiated thymidine triphosphate. Reduction in the count of 50% or more in the test is noted as inhibitory activity.

Virus preparation: Pre-titrated HBsAg and HBeAg positive serum was centrifuged at 35,000 rpm for 3 hrs using SW 41 rotor. The pellet was washed in PBS and again centrifuged at 35,000 rpm. The pellet got in this was dissolved in PBS and stored at −20° C.

Procedure: The procedure followed was as described by Lofgren et al (1989). Prior to the assay, the virus preparation was pre-treated with ⅛ volume of 2% mercapto ethanol and 10% NP-40 for 15–30 min at room temperature. Aliquotes of 25 μl were then incubated at 37° C. for 3 hrs together with 25 μl reaction mixture containing Tris-HCl (pH 8.0) 100 mM, $MgCl_2$ 20 mM, KC 200 mM, dNTPs 10 mM each and $^3$H dTTP 10 mM and 25 μl of DNase and RNase free water and the formulation of the present invention which is to be studied. After incubation, to 50 μl of reaction mixture 10 μl of 0.2M EDTA was added and spotted onto a Whatmnan DE81 filter paper discs and processed for a radioactivity measurement.

The results of the assays of the pharmaceutical formulation of the present invention prepared by the process described in the Examples 1 to 8 are given in Table 5.

C. Reverse Transcriptase Inhibiting Property of the Pharmaceutical Formulation of the Invention This Property Was Evaluated by Electrophoretic and Isotopic RT-Inhibition Assays Electrophoretic RT-Inhibition Assay The electrophoretic RT-inhibition was conducted to screen and identify the anti-retroviral potentials of formulations of the present invention prepared by the process described in Examples 1 to 8. Moloney murine leukaemia virus reverse transcriptase (MMLV RT) was used for CDNA synthesis.

Principle: Reverse transcriptase (RNA-dependent DNA polymerase) is an enzyme in retroviruses and plays an important role in their multiplication by transcribing the viral RNA into cDNA which is required for the proviral synthesis. This test is performed to find the ability of an extract to inhibit RT. The presence of this property is determined by the formation or non-formation of cDNA.

Procedure: The electrophoretic RT-inhibition assay was performed in a reaction mixture that contained the following in a final volume of 25 μl. Tris HCl (pH 8.3) 50 mM, $MgCl_2$ 6 mM, KCl 40 mM, P(rA)(dT)$_{12-18}$ 0.5 μg, MMLV RT 5 Units. To this 2 μl of the formulation of the present invention prepared by the process described in the Examples 1 to 10 was added immediately before incubation. A positive control and solvent control were set up using Azidothymidine (1 μg/ml) and the solvent used for reconstitution of extract, respectively. All the tubes were incubated at 37° C. for one hour, and the reaction was stopped using 0.1 M EDTA. 10 μl of each assay mix was loaded onto a 1% gel and run for 30 minutes at 60 V. The gel was stained in Ethidium bromide (0.5 μg/ml) and viewed in UV transilluminator. The presence of absence of the cDNA band indicates the non-inhibition of inhibition of RT respectively. Each sample was tested three times for the reproducibility of its activity if present. The procedure followed is a modification of cDNA synthesis kit procured from Amersham International Ltd. Burminghamshire, UK.

Isotopic Enzyme Assays

Standard Isotopic RT-Inhibition Assay

Principle: as described in the electrophoretic RT-inhibition assay. The inhibitory activity is identified by using an isotope, tritiated thymidine triphosphate. A 50% or more reduction in the radioisotope uptake between the control and the test is taken as a positive inhibitory activity.

Procedure: The procedure followed was as described by Ono et al. (1989). The assay was performed in a reaction mixture that contained the following in a final volume of 50 μl. Tris HCl 50 mM, P(rA)(dT)$_{12-18}$ 10 μl/ml, BSA 10 μg/ml, $^3$H-dTTP 0.5 mM, DTT 10 mM, $MgCl_2$ 3 mM, MMLV RT 1 unit.

In the test, a known concentration of the formulation of the present invention prepared by the process described in the Examples 1 to 8 was added to the reaction mixture and incubated. Similarly a positive control (0.1 μg/ml AZT), a negative control (distilled water) and a solvent control (solvent used in extract) were set up. Each set of test and controls were run in triplicate. After 30 minutes the reaction was stopped by adding 10 μl of ice cold EDTA (0.2M) and immersing the mixture in ice immediately.

Processing for Radioactivity Measurement

After termination of the reaction, the DNA was precipitated using 10 μl of cold 5% TCA and 0.1 M sodium pyrophosphate. 50 μl of the reaction mixture was then filtered through Whatman DE81 filter paper. The filter paper was later washed thrice in 3 ml of 5% TCA and three times in absolute alcohol. The filters were then air dried, and radioactivity measured using a toluene-based scintillation cocktail. A reduction of 50% of more in the radioactive count of the test from the negative control is taken as presence of RT inhibition activity. The results are presented in Table 5.

D. Anti Hepatotoxic Potentials of the Pharmaceutical Formulation of the Present Invention Anti hepatotoxic potentials of formulation of the present invention prepared by the process described in the Examples 1 to 8 was assessed after challenging isolated rat hepatocytes with a known hepatotoxic compound β-galactosoamine.

Isolation of Rat Hepatocytes

An adult rat of known weight preferably more than 125 gm was anaesthetized with ether and a midline incision were made. The liver was perfused through the portal vein with 30–50 ml of cold sodium citrate (0.027M) in calcium free lockets solution. During the perfusion, the liver gets blanched and fully distended. Perfusion is generally completed within 5 minutes of anaesthetizing the animal. The perfused liver is excised and washed well with the perfusion fluid and pressed in folds of sterile filter paper, weighed and cut into several small pieces and with a pair of scissors. A known wet weight of the liver (usually between 2–6 gm) was transferred with 5 volume of cold 0.25M sucrose into a sterile glass homogenizer and finely grounded. The cell suspension was filtered once, without application of pressure through 200-mesh brass gauze to remove strands of connective tissue and clumps of cells. The suspension contained some cell debris and blood cells at this stage, which were removed by centrifugation at a low speed (100–200 g) for 2 minutes. After removal of the supernatant, the cell sediment was resuspended in a known volume of the minimum essential medium for further studies.

Cell Count

100 μl of the cells are taken and to this 300 μl of 4% trypan blue is added and this is mixed and then viewed in the haemocytometer within 5 minutes of staining. The cells, which have not taken the dye, are live cells, which are counted.

The cells were inoculated into the culture medium which is composed of Eagle's MEM supplemented with 10% heat inactivated calf serum penicillin (100 IU/ml), streptomycin (100 IU/ml), 10–6M Dexamethosome and 10–8 units Insulin. Inocula of $5 \times 10^4$ cells /0.1 ml/cm$^3$ were seeded into plastic dishes and preincubated in a humidified incubator at 37° C. under 5% $CO_2$ in air for 24 hours and medium is replaced.

Study Design

Four sets of isolated rat hepatocyte cultures were put up. Set I acted as control, Set II was treated with 1 mg/ml concentration of the formulation of the present invention prepared by the process described in the Examples 1 to 8. Set III with 0.5 mM concentration of β-galactosamine, a known hepatotoxic agent and set IV was treated with β-galactosamine and then protected with the formulation of the present invention. Culture supermatants of all the sets were assayed for glutamic pyruvate transaminase levels as per standard procedures.

Results

1. The study revealed that the formulation of the present invention by itself did not bring about any hepatotoxicity on rat hepatocytes,
2. β-galactosamine was proved as a profound hepatotoxic chemical.
3. The formulation of the present invention at 1 mg/ml concentration was shown to protect isolated rat hepatocytes significantly from β-galactosamine induced hepatotoxicity.
4. Thus the study has proved that the formulation of the present invention has significant antihepatoxic potentials (p<0.01).

The results of the assay by the different formulations of the present invention prepared by the process described in the Examples 1 to 8 are given in Table 5.

E. Invitro Inhibition of HBSAG Secretion by the Pharmaceutical Formulation of the Present Invention Alexander cell line (345) was kindly provided by Dr. Tim Harnson, Academic School of Medicine, Royal Free Hospital, London which is a continues cell line of human hepatic cellular carcinoma cells (PLC/PRF/5). The cell line was cultured from a cancer patient who was also an HBsAg carrierser. These cells grown in vitro secrete only HBsAg without any infectious virus.

Cultivation of Alexander Cell Line

Alexander cell line was grown as per the procedure adopted for the cultivation of Vero cell line described in section 4.6.2.2. 10% foetal calf serum (Sigma Chemical Company, USA) was used instead of 5% inactivated goat serum.

Study Design

Six sets of Alexander cell line were grown in Leighton tubes. On day 1 of the experiment, the culture medium was decanted, and fresh medium was added. 1 mg/ml concentration of formulation of the present invention prepared by the process described in the Examples 1 to 8 was added to each tube. The culture medium (supernatant) was assayed daily at varying doubling dilutions starting from neat t 1/128 dilution to check for the inhibition of secretion of HBsAg by the cell line. Distilled water was added to the control tubes. HBsAg detection from the supernatant was done using Hepanostika HBsAg kits as per the procedure described earlier.

Results

Inhibition of HBsAg secretion was observed for 48 hours when the cell line was treated with 1 mg/ml concentration of the formulation as a single dose. However HBsAg was detected from the culture medium at lower dilutions after 72 hours. The details of the results of the formulations of the present invention prepared by the process described in the examples 1 to 10 are given in Table 5.

F. Study of Immunomodulatory Potentials of the Pharmaceutical Formulation of the Present Invention (a) The isolation of lymphocytes was done by ficoll-paque method using 0 group Rh+ve human blood. After centrifugation of the blood sample layered onto the Ficoll-paque at 400 g for 20 min at 18–20° C. in a refrigerated centrifuge, lymphocytes are seperated and suspended gently in 6–8 ml of balanced salt solution. It was centrifuged at 1o0g for 10 min at 18–20° C. After removing the supernatant, the lymphocytes are suspended in RPMI medium.

(b) Lymphocyte viability test: A cell suspension containing 5×10-6 cells/ml was prepared in RPMI medium. 0.5 ml of 0.4% trypan blue solution was transferred to a test tube. To this 0.3 ml of RPMI medium and 0.2 ml of cell suspension were added and mixed thoroughly. The mixture was allowed to stand for 5 minutes. The suspension was viewed through a haemocytometer and looked for viable cells. The viable cells do not take up the dye.

$$\% \text{ Viability was calculated by the formula} = \frac{\text{total viable cells (unstained)}}{\text{total cells (stained \& unstained)}} \times 100$$

(c) T-cell proliferation assay: To test by in-vitro method the T-cell proliferation inhibition/acceleration potentials of formulation of the present invention prepared by the process described in the Examples 1 to 8, which may be indicative of immunomodulatory potentials.

Requirements for the Assay

1. Peripheral blood lymphocytes (PBL)
2. Phytohaemagglutinin (PHA)
3. KrT (3,4,5-dimethyl thyol-2-yl-di phenyl tetrazolium bromide)
4. Add propanol (0.40M Ha in isopropanol)
5. RPMI 1640 medium
6. Fetal calf serum
7. Antibiotics Vancomycin—25ug/ml Gentamycin—20µg/ml Procedure of the Assay 1. Peripheral blood lymphocytes (PBL) were obtained by the Ficoll-hypaque method
2. Under sterile condition 50 µl of PBL suspension (5×106 cells/ml), Sopl of sample dilutions and 50 µl of PHA (33µg/ml) were added in the 96-well flat bottomed microtitre plate
3. Incubate the plates at 37° C. and 5% $CO_2$ for 48 hrs
4. After incubation cell growth was quantified by adding 25 µl of MTT to each well
5. Incubate the plates at 37° C. for 4 hrs
6. 50 µl of acid propanol was added and the content of each well was mixed thoroughly
7. Plates were read on automatic ELISA reader at 550 nm.

Controls & Tests in Duplicate

| | |
|---|---|
| 1. PBA + PHA | → 100% activity |
| 2. PBL + RPMI | → 0% activity |
| 3. PBL + Picroliv | → known Positive control |
| 4. PBL + formulations of the present invention | → Test samples |

Results

The extracts were assessed for the lymphocyte proliferation activity by a) Microscopic: Multiwell plates were observed under inverted phase contrast microscope for any observable induction of proliferation. A minimum of 10 fields was observed.

b) MTT calorimetric assay: The multiwell plates were incubated with MTT for 4 hrs. Then the plates were centrifuged at 100 rpm for 10 min. The supernatant was aspirated, 50 µl of acid propanol was added and the content of each well was mixed thoroughly. The plates were read in an automated ELISA reader at 550 nm. The proliferation of the lymphocytes was assessed by comparing with known immunomodulatory control (Picroliv).

The details of the results are given in Table 5.

TABLE 5

ANTIVIRAL AND BIOLOGICAL EFFICACY OF THE FORMULATIONS OBTAINED BY THE PROCESS DESCRIBED IN EXAMPLES 1 TO 10

ANTIVIRAL & BIOLOGICAL PROPERTIES (MIC/ml concentration)

| EXAMPLES | HBsAg binding | HBV-DNAp inhibition | RT-inhibition | Inhibition of HBsAg secretion | Amt-hepatotoxicity | Immunomodulation |
|---|---|---|---|---|---|---|
| Example-1 | 2.5 mgm | 400 µg | 200 µg | 1 mgm | 1 mgm | 400 µg |
| Example-2 | 1.25 mgm | 100 µg | 100 µg | 0.5 mgm | 1 mgm | 100 µg |

TABLE 5-continued

ANTIVIRAL AND BIOLOGICAL EFFICACY OF THE FORMULATIONS
OBTAINED BY THE PROCESS DESCRIBED IN EXAMPLES 1 TO 10

ANTIVIRAL & BIOLOGICAL PROPERTIES (MIC/ml concentration)

| EXAMPLES | HBsAg binding | HBV-DNAp inhibition | RT- inhibition | Inhibition of HBsAg secretion | Amt- hepatotoxicity | Immunomodulation |
|---|---|---|---|---|---|---|
| Example-3 | 2.5 mgm | 400 μg | 200 μg | 1 mgm | 1 mgm | 400 μg |
| Example-4 | 1.25 mgm | 200 μg | 100 μg | 1 mgm | 1 mgm | 200 μg |
| Example-5 | 5.0 mgm | 400 μg | 400 μg | 2 mgm | 1 mgm | 400 μg |
| Example-6 | 2.5 mgm | 200 μg | 100 μg | 1 mgm | 1 mgm | 200 μg |
| Example-7 | 2.5 mgm | 400 μg | 200 μg | 2 mgm | 1 mgm | 400 μg |
| Example-8 | 1.25 mgm | 200 μg | 100 μg | 1 mgm | 1 mgm | 200 μg |
| Example-9 | 2.5 mgm | 400 μg | 400 μg | 2 mgm | — | — |
| Example-10 | 5 0 mgm | — | — | — | 1 mgm | 400 μg |

Table 6 summarises the case studies on the efficacy of the new formulation of the present invention prepared by the process described in Example 1 for the treatment of acute and chronic Hepatitis C infeons conducted at Chennai, Indiaby Thyagarajan et al (1996–99) using the formulation

TABLE 6

Case studies on the efficacy of the new formulation of P. amarus for the treatment of
acute and chronic Hepatitis C infections conducted at Chennal, India using the
formulation obtained by the process described in Example 1 (Thyagarajan et al, unpublished)

| Sl. No | Pt. Identity | Age/Sex | Diagnosis & History | HCV Ab | HCV RNA | SGOT IU | SGPT IU | SAP IU | S. bilirubin Mgm % |
|---|---|---|---|---|---|---|---|---|---|
| 1 | Mrs. M | 45/F | PTH B&C After cardiac surgery | + | + | 210 | 322 | 78 | 5.6 |
| 2 | Mrs. U.B | 42/F | PTH-C CPH after caesarian | + | ND | 200 | 146 | 80 | 0.6 |
| 3 | Mr. V.R | 52/M | PTH-C CLD Cardiac surgery | + | ND | 237 | 290 | 34 | 14.3 |
| 4 | Mrs. L.M | 38/F | PTH-C AVH | + | + | 562 | 360 | 34 | 0.9 |
| 5 | Mrs. V.O | 44/F | PTH-B&C AVH | + | + | 111 | 173 | 44 | 0.9 |
| 6 | Mrs. J.A | 61/F | PTH-C AVH | + | + | 162 | 213 | 123 | 0.9 |
| 7 | Mrs. R.K | 38/F | CAH Surgery+ Transfusion+ | + | + | 404 | 581 | 88 | 1.5 |
| 8 | Mr. R.I.R | 32/M | PTH-C | + | + | 52 | 95 | 201 | 0.6 |
| 9 | Mr. G.N | 37/M | Cirrhosis (B&C) Transfusion+ Surgery+ Jaundice+ | + | ND | 60 | 100 | 444 | 13 |
| 10 | Mr. B.M | 24/M | Recurrent VH | + | − | 69 | 108 | ND | 3.1 |
| 11 | Mrs. M.K | 29/F | PTH-AVH-C Surgery+ | + | + | 250 | 90 | ND | 5.7 |
| 12 | Mr. SMAW | 45/M | CLD | + | + | 76 | 47 | 127 | 1.9 |
| 13 | Mr. R | 25/M | PTH-AVH-C Blood Trans+ | + | ND | 79 | 111 | – | 2.4 |
| 14 | Mr. K.P.J | 63/M | PTH-AVH-C Surgery+ Blood trans+ | + | ND | 207 | 233 | 280 | 1.6 |
| 15 | Mr. S.V | 29/M | CRF: Dialysis | + | + | 185 | 509 | 376 | 0.7 |
| 16 | Mr. M.C | 55/M | CAH | + | + | 27 | 125 | 139 | 1.2 |
| 17 | Dr. S.K | 29/M | Asymptomatic C? occupational | + | + | 52 | 66 | 72 | 0.6 |
| 18 | Mrs. V.R | 50/F | PTH-AVH-C Blood trans+ | + | ND | 482 | 809 | 62 | 18.6 |

TABLE 6-continued

| Sl. No | P. amarus treatment period (months) | HCV Ab | HCV RNA | SGOT IU | SGPT IU | SAP IU | S. bilirubin Mgm % |
|---|---|---|---|---|---|---|---|
| 1 | 2 m | + | – | 25 | 34.2 | 44 | 1.2 |
| 2 | 9 m | + | ND | 69 | 72 | 22 | 0.6 |
| 3 | 3 m | + | ND | 45 | 62 | 12 | 2.8 |
| 4 | 3 m | + | – | 62 | 48 | 18 | 0.8 |
| 5 | 4 m | + | – | 55 | 42 | 20 | 0.8 |
| 6 | 3 m | + | + | 112 | 146 | 84 | 0.9 |
| 7 | 6 m | + | + | 340 | 491 | 52 | 0.5 |
| 8 | 3 m | + | + | 42 | 38 | 62 | 0.5 |
| 9 | 6 m | + | ND | 56 | 72 | 120 | 5.2 |
| 10 | 9 m | + | – | 35 | 24 | – | 1.0 |
| 11 | 5 m | + | + | 46 | 42 | ND | 1.8 |
| 12 | 6 m | + | + | 72 | 44 | 86 | 1.9 |
| 13 | 3 m | + | ND | 42 | 35 | – | 0.9 |
| 14 | 3 m | + | ND | 48 | 42 | 51 | 0.9 |
| 15 | 3 m | + | + | 61 | 85 | 78 | 0.7 |
| 16 | 6 m | + | + | 20 | 54 | 115 | 0.9 |
| 17 | 6 m | + | + | 38 | 55 | 42 | 0.56 |
| 18 | 3 m | + | ND | 83 | 128 | 40 | 4.0 |

Inference: Total cases studied: 18; Normalisation of enzymes: 14/18 (77.8%); HCV-RNA negativity: 4/12 (33.3%) (By Qualitative PCR only) Physical well being and clinical improvement 17/18 (94.4%); Observable side effects: nil [Dosage: 500 mgms oral capsules of P.amarus-formulation (Example 1 × thrice daily × peroids mentioned against each case]

In summary, the above findings confirm that when parts of medicinal plant, Phyllanthus amarus are extracted separately with a polar solvent alone, polar solvent and water in specific ratios and when such extracts are mixed together, the resultant formulation has all the essential antiviral and biological properties while the individual polar or aqueous extracts alone does not possess one or more of these properties.

It is our finding that if all the above said essential properties are made available in a single formulation, the resulting formulation will have uniform and stable antiviral and biological properties.

G. Biological and Chemical Standardisation of the Pharmaceutical Formulation of the Present Invention As the antiviral activity of P.amarus was found to differ between collections made from different areas, the formulation preparation to be used in the clinical trial was standardized by evaluating their antiviral properties and matching them using the HPLC pattern upon fractionation, initially and later upon the preparation of the pharmaceutical formulations of the present invention prepared by the process mentioned in Examples 1 to 8.

Collection of plant material: Phyllanthus amarus was collected from different places within Chennai city and within Tamilnadu and Bangalore. They were Salem, Mathuranthagam, Coimbatore, Tiruchy, Tiruttani, Bangalore from outside Madras; Annanagar, Thiruvanmiyur and Tiruvatriyur from in and around Madras. All these plant materials were identified based on the taxonomical system of nomendature.

Preparation of the Formulation for HPLC

The formulations of the present invention prepared by the process explained in Examples 1 to 8 from various collections as described earlier under the head "embodiments". The formulations so obtained were filtered and made upto 50 ml. 10 ml of each extract was used as such for chemical standardisation study. The rest was dried and used for antiviral and biological testing by a battery of tests as described in A to F. Chemical fingerprinting was performed using a High performance liquid chromatogram for each of the extract and formulation.

HPLC analysis

Requirements
1. HPLC grade methanol
2. HPLC grade water
3. Shimpack PrepODS(K) kit (4.6 mmid×25 cm, particle dia 5 pm Rreverse phase column) (procured from Shimadzu Asia Pacific PTE ltd., Singapore)

Equipment Required

Figure 2:
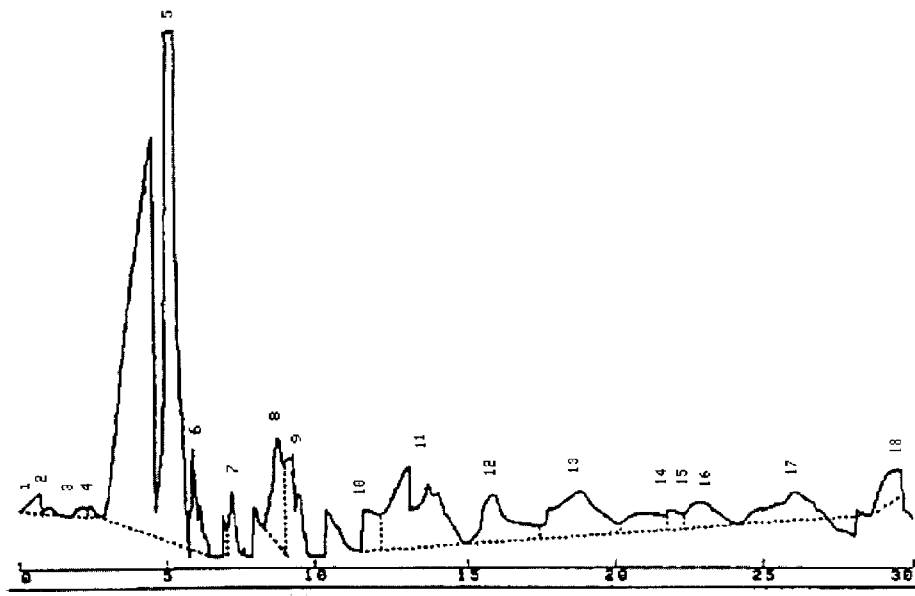
FIG. 2 depicts the HPLC pattern of the formulation that was prepared by the process that is described in Example 2.
Figure 3:
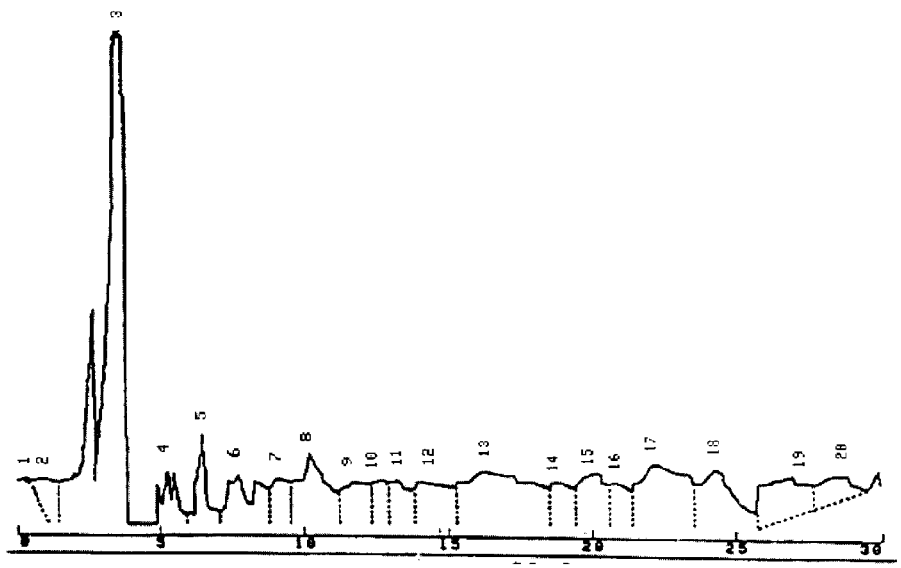
FIG. 3 depicts the HPLC pattern of the formulation that was prepared by the process that is described in Example 3.
Figure 4:
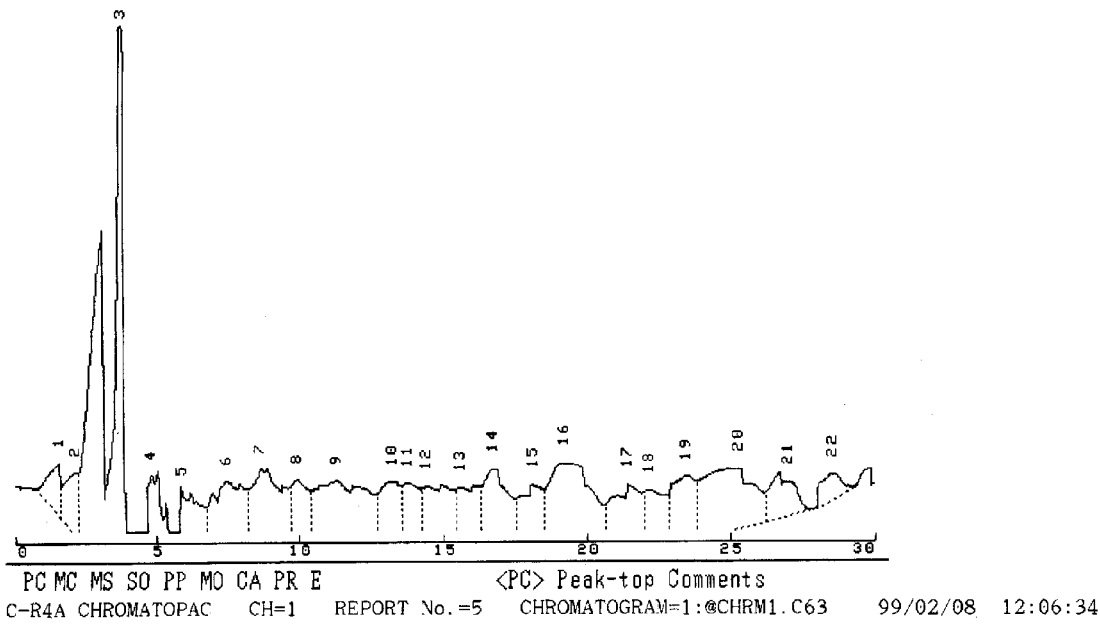
FIG. 4 depicts the HPLC pattern of the formulation that was prepared by the process that is described in Example 4.
Figure 5:
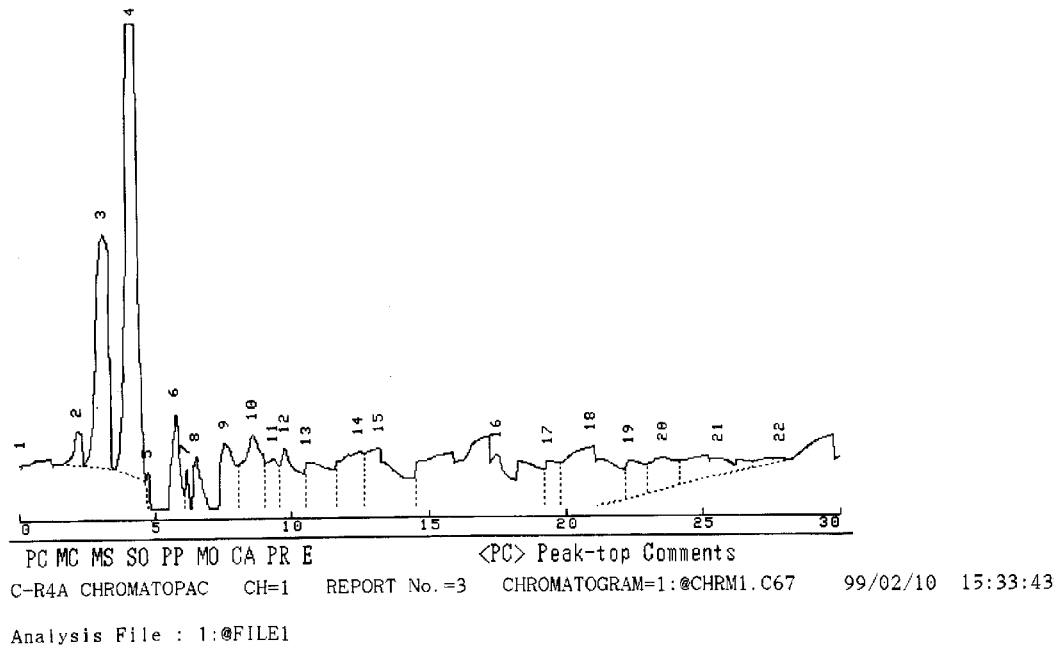
FIG. 5 depicts the HPLC pattern of the formulation that was prepared by the process that is described in Example 5.
Figure 6:
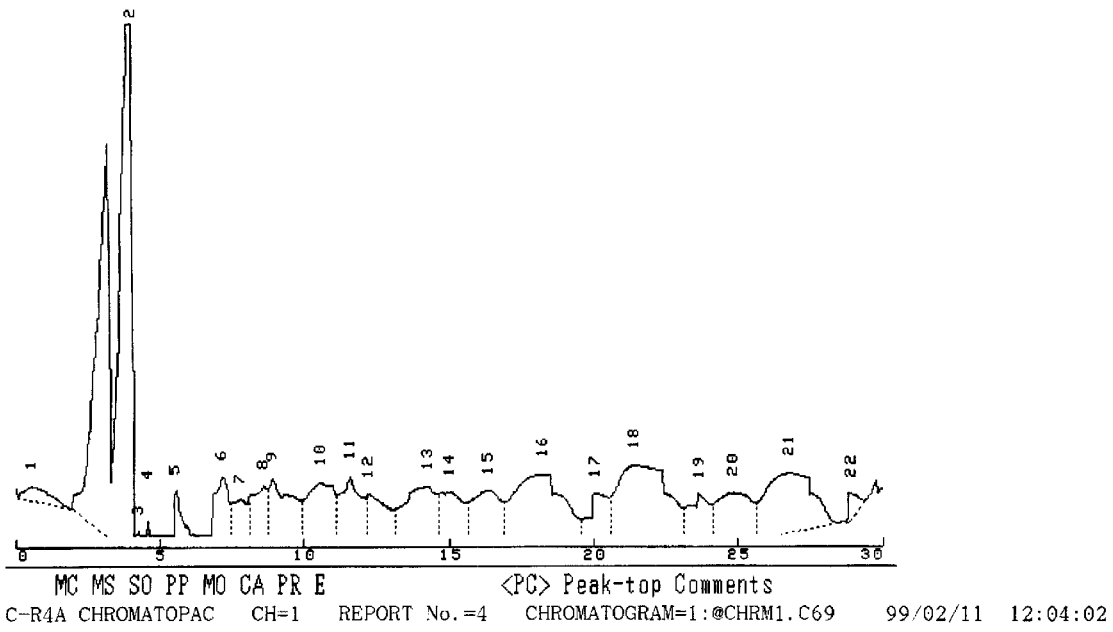
FIG. 6 depicts the HPLC pattern of the formulation that was prepared by the process that is described in Example 6.
Figure 7:
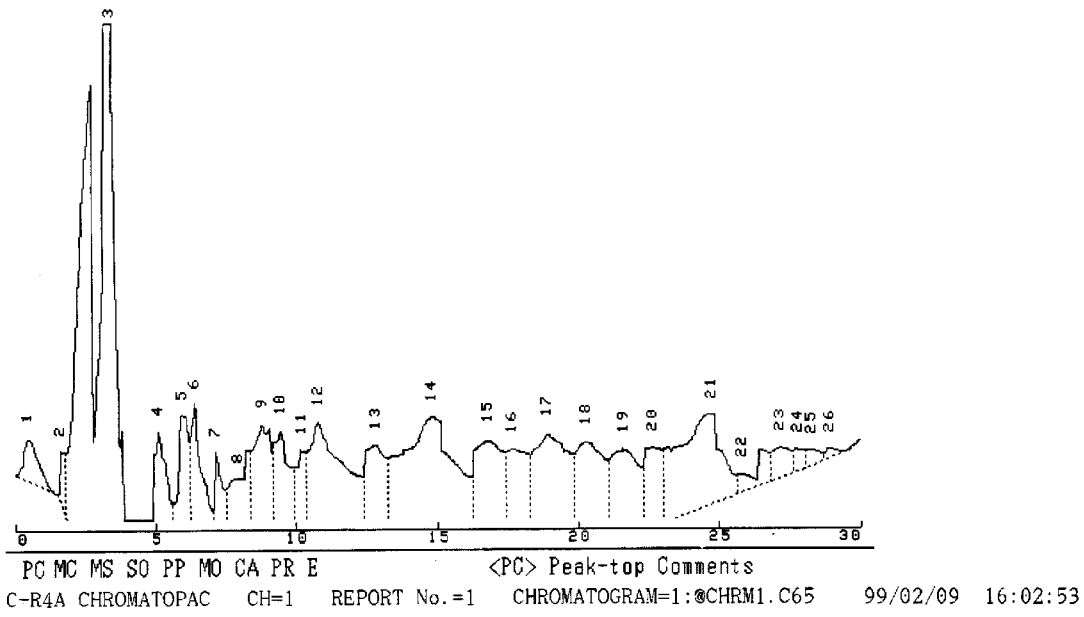
FIG. 7 depicts the HPLC pattern of the formulation that was prepared by the process that is described in Example 7.
Figure 8:
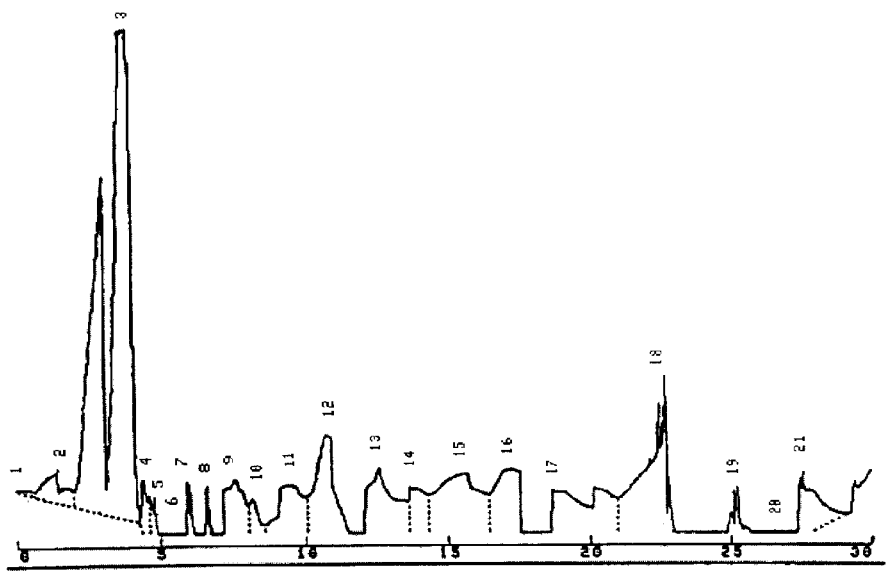
FIG. 8 depicts the HPLC pattern of the formulation that was prepared by the process that is described in Example 8.
Figure 9:
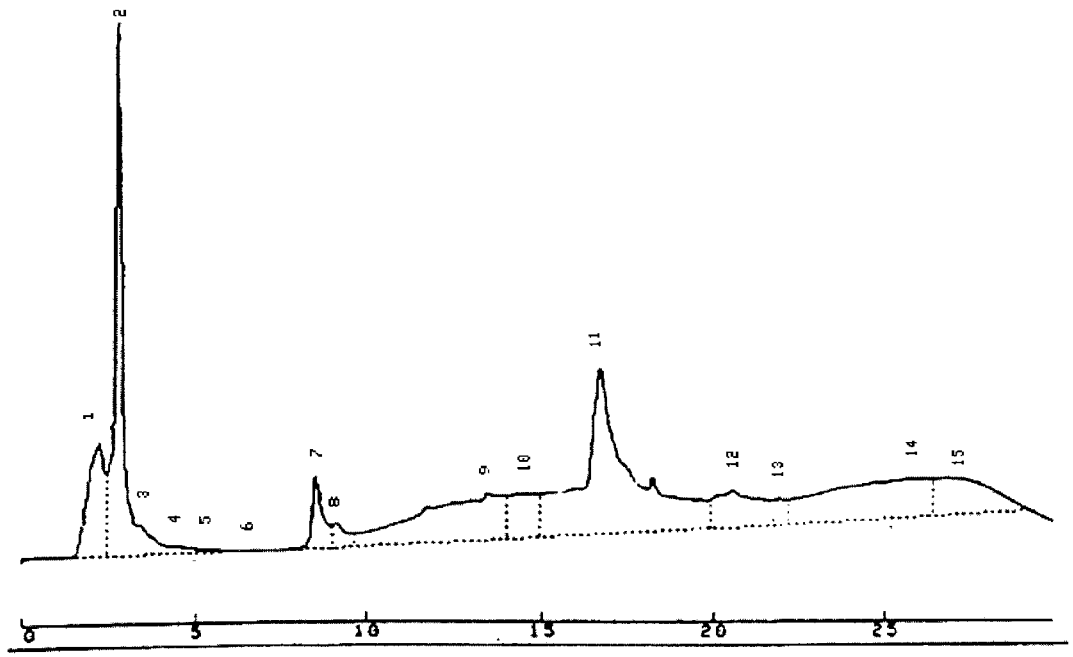
FIG. 9 depicts the HPLC pattern of the formulation that was prepared by the process that is described in Example 9.
Figure 10:
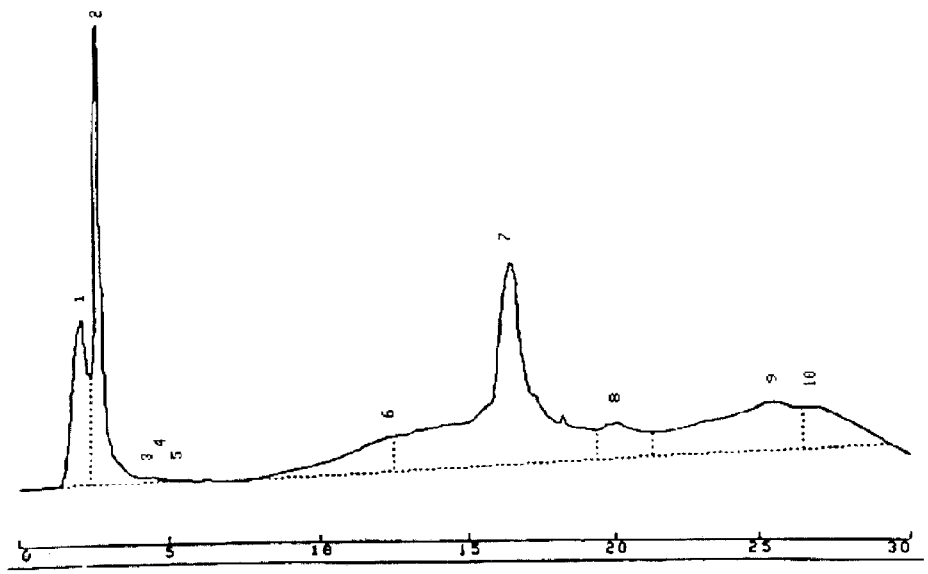
FIG. 10 depicts the HPLC pattern of the formulation that was prepared by the process that is described in Example 10.

HPLC-A Shimadzu chromatographic system comprising
1. LC-6A liquid pump
2. SCL-6B system controller
3. Model 7125 injector
4. SPD6A UV detector Chromatgraphic System Column: Shimpack PrepODS (K) kit (4.6 mmid×25 cm, particle dia 5-pm Reverse phase column)
Mobile phase: Methanol:water gradient
Flow rate: 2 ml/min
Detection: UV 225 nm
Injection volume: 10 μl Procedure: The formulations of the present invention prepared for the study was filtered through 0.2μ membrane filter discs. The filtrate was used for the study. After the column was washed, to achieve a baseline, the gradient parameters were set and the run was started by injecting 10 μl of the formulation. The chromatogram was plotted. Similarly chromatographic patterns were plotted for all the formulations. The chromatograms got were compared and analysed for their matching antiviral and biological properties as described in A to F. The formulations prepared as per the process explained in Examples 1 to 8 were found to have all the above mentioned properties optimally as shown in Table 6 and to possess the HPLC pattern depicted in FIG. 1 to 10 of the drawings accompanying this specification which represents the HPLC pattern of the formulation prepared by the process described in Example 1 to 10.

The pharmaceutical formulation of the present invention can be administered to a person who requires such administration by the normal means such as tablets, capsules, oral suspensions and the like. The dosage of administration of the formulation may range from 250 mg to 500 mg thrice daily for a duration of 1 to 6 months time depending upon the clinical conditions of the person who requires the administration of the formulation Advantages of the Invention The pharmaceutical formulation of the present invention can find applications for the treatment of acute and chronic Hepatitis B, acute and chronic Hepatitis C and other related viral infections of the liver because 1. The formulation has all the essential antiviral and biological properties against Hepatitis B virus; Hepatitis C virus and other related viral infections of the liver.
2. The formulation is non-toxic at tissue and cellular level; with proven safety for human use by experimental studies and clinical trials.
3. The formulation possess reproducible clinical efficacy in the treatment of acute and chronic Hepatitis B; acute and chronic Hepatitis C and other related viral infections of the liver.

What is claimed is:

1. A pharmaceutical formulation useful for treating acute Hepatitis B, chronic Hepatitis B, acute Hepatitis C, chronic Hepatitis C, and/or other related viral infections of a liver, the pharmaceutical formulation comprising an Extract 1, an Extract 2, and an Extract 3, wherein:
   (i) the Extract 1 is an extract of a first amount of a plant *Phyllanthus amarus* obtained by using a first polar solvent alone, wherein the first polar solvent comprises a polar solvent other than water;
   (ii) the Extract 2 is an extract of a second amount of the plant *Phyllanthus amarus* obtained by using a mixture of a second polar solvent and water alone, wherein the second polar solvent comprises a polar solvent other than water; and
   (iii) the Extract 3 is an extract of a third amount of the plant *Phyllanthus amarus* obtained by using water alone.

2. A pharmaceutical formulation as claimed in claim 1 which comprises:
   (i) 10 to 40% w/w of the Extract 1;
   (ii) 10 to 40% w/w of the Extract 2, wherein a ratio of the second polar solvent to the water in the mixture of the second polar solvent and the water ranges from 20:80% w/w to 80:20% w/w; and
   (iii) 10 to 40% w/w of the Extract 3.

3. A pharmaceutical formulation as claimed in claim 1 which comprises:
   (i) 20 to 30% w/w of the Extract 1;
   (ii) 20 to 40% w/w of the Extract 2, wherein a ratio of the second polar solvent to the water in the mixture of the second polar solvent and the water ranges from 80:20% w/w to 20:80% w/w; and
   (iii) 20 to 30% w/w of the Extract 3; and
wherein the pharmaceutical formulation further comprises 20 to 40% w/w of an Extract 4, wherein the Extract 4 is an extract of a fourth amount of the plant *Phyllanthus amarus* obtained by using a second mixture of a third polar solvent and water alone, wherein a ratio of the third polar solvent to the water in the second mixture ranges from 20:80% w/w to 80:20% w/w, and wherein the third polar solvent comprises a polar solvent other than water.

4. A pharmaceutical formulation as claimed in claim 1 which comprises one part by volume of each of:
   (i) the Extract 1;
   (ii) the Extract 2; and
   (iii) the Extract 3.

5. A pharmaceutical formulation as claimed in claim 1 which comprises one part by volume of each of:
   (i) 10 to 40% w/w of the Extract 1;
   (ii) 10 to 40% w/w of the Extract 2, wherein a ratio of the second polar solvent to the water in the mixture of the second polar solvent and the water ranges from 20:80% w/w to 80:20% w/w; and
   (iii) 10 to 40% w/w of the Extract 3.

6. A pharmaceutical formulation as claimed in claim 1 which comprises one part by volume of each of:
   (i) 20 to 30% w/w of the Extract 1;
   (ii) 20 to 40% w/w of the Extract 2, wherein a ratio of the second polar solvent to the water in the mixture of the second polar solvent and the water ranges from 80:20% w/w to 20:80% w/w; and
   (iii) 20 to 30% w/w of the Extract 3; and
wherein the pharmaceutical formulation further comprises one part by volume of:
   (iv) 20 to 40% w/w of an Extract 4, wherein the Extract 4 is an extract of a fourth amount of the plant *Phyllanthus amarus* obtained by using a second mixture of a third polar solvent and water alone, wherein a ratio of the third polar solvent to the water in the second mixture ranges from 20:80% w/w to 80:20% w/w, and wherein the third polar solvent comprises a polar solvent other than water.

7. A pharmaceutical formulation as claimed in claim 1 which comprises two parts by volume of:
   (i) the Extract 1; and
one part by volume of each of:
   (ii) the Extract 2; and
   (iii) the Extract 3.

8. A pharmaceutical formulation as claimed in claim 1 which comprises two parts by volume of:
   (i) 10 to 40% w/w of the Extract 1; and
one part by volume of each of:
   (ii) 10 to 40% w/w of the Extract 2, wherein a ratio of the second polar solvent to the water in the mixture of the second polar solvent and the water ranges from 20:80% w/w to 80:20% w/w; and
   (iii) 10 to 40% w/w of the Extract 3.

9. A pharmaceutical formulation as claimed in claim 1 which comprises two parts by volume of:
   (i) 20 to 30% w/w of the Extract 1; and
one part by volume of each of:
   (ii) 20 to 40% w/w of the Extract 2, wherein a ratio of the second polar solvent to the water in the mixture of the second polar solvent and the water ranges from 80:20% w/w to 20:80% w/w; and
   (iii) 20 to 30% w/w of the Extract 3; and
wherein the pharmaceutical formulation further comprises one part by volume of:
   (iv) 20 to 40% w/w of an Extract 4, wherein the Extract 4 is an extract of a fourth amount of the plant *Phyllanthus amarus* obtained by using a second mixture of a third polar solvent and water alone, wherein a ratio of the third polar solvent to the water in the second mixture ranges from 20:80% w/w to 80:20% w/w, and wherein the third polar solvent comprises a polar solvent other than water.

10. A pharmaceutical formulation as claimed in claim 1, wherein the pharmaceutical formulation has all the following properties:
   (a) HBsAg binding property facilitating inactivation of virus in circulation ultimately leading to viral clearance;
   (b) HBV-DNA polymerase enzyme inhibiting potential, thus acting as anti-viral and preventing multiplication of HBV;
   (c) reverse transcriptase enzyme inhibition for inhibition of HBV replication;
   (d) inhibition of HBsAg secretion from HBV transinfected liver cells thus possessing activity against virus-infected chronic liver disease conditions;

(e) hepato-protective, anti-inflammatory, anti-hepatotoxic and liver-cell regenerative properties against liver-cell toxicity brought about by one or more hepatitis viruses or other hepatotoxic agents; and (f) immunomodulating property to potentiate an immune system of an HBV/HCV-infected patient towards virus clearance and protective-antibody responses, wherein protective-antibody responses may include anti-HB's.

11. A pharmaceutical formulation as claimed in claim 3, wherein the first amount of the plant *Phyllanthus amarus* is a first powder of the plant *Phyllanthus amarus;* wherein the second amount of the plant *Phyllanthus amarus* is a second powder of the plant *Phyllanthus amarus;* wherein the third amount of the plant *Phyllanthus amarus* is a third powder of the plant *Phyllanthus amarus;* and wherein the fourth amount of the plant *Phyllanthus amarus* is a fourth powder of the plant *Phyllanthus amarus.*

12. A pharmaceutical formulation as claimed in claim 1 which comprises one part by volume of each of:

(i) 20 to 30% w/w of the Extract 1;

(ii) 20 to 40% w/w of the Extract 2, wherein a ratio of the second polar solvent to the water in the mixture of the second polar solvent and the water ranges from 80:20% w/w to 20:80% w/w; and (iii) 20 to 30% w/w of the Extract 3.

13. A pharmaceutical formulation as claimed in claim 1 which comprises two parts by volume of:

(i) 20 to 30% w/w of the Extract 1; and one part by volume of each of:

(ii) 20 to 40% w/w of the Extract 2, wherein a ratio of the second polar solvent to the water in the mixture of the second polar solvent and the water ranges from 80:20% w/w to 20:80% w/w; and (iii) 20 to 30% w/w of the Extract 3.

14. A process for preparing a pharmaceutical formulation useful for treating acute Hepatitis B, chronic Hepatitis B, acute Hepatitis C, chronic Hepatitis C, and/or other related viral infections of a liver, the process comprising mixing an Extract 1, an Extract 2, and an Extract 3, wherein:

(i) the Extract 1 is an extract of a first amount of a plant *Phyllanthus amarus* obtained by using a first polar solvent alone, wherein the first polar solvent comprises a polar solvent other than water;

(ii) the Extract 2 is an extract of a second amount of the plant *Phyllanthus amarus* obtained by using a mixture of a second polar solvent and water alone, wherein the second polar solvent comprises a polar solvent other than water; and (iii) the Extract 3 is an extract of a third amount of the plant *Phyllanthus amarus* obtained by using water alone.

15. A process as claimed in claim 10 which comprises mixing:

(i) 10 to 40% w/w of the Extract 1;

(ii) 10 to 40% w/w of the Extract 2, wherein a ratio of the second polar solvent to the water in the mixture of the second polar solvent and the water ranges from 20:80% w/w to 80:20% w/w; and (iii) 10 to 40% w/w of the Extract 3.

16. A process as claimed in claim 14 which comprises mixing:

(i) 20 to 30% w/w of the Extract 1;

(ii) 20 to 40% w/w of the Extract 2, wherein a ratio of the second polar solvent to the water in the mixture of the second polar solvent and the water ranges from 80:20% w/w to 20:80% w/w; and (iii) 20 to 30% w/w of the Extract 3; and wherein the pharmaceutical formulation further comprises 20 to 40% w/w of an Extract 4, wherein the Extract 4 is an extract of a fourth amount of the plant *Phyllanthus amarus* obtained by using a second mixture of a third polar solvent and water alone, wherein a ratio of the third polar solvent to the water in the second mixture ranges from 20:80% w/w to 80:20% w/w, and wherein the third polar solvent comprises a polar solvent other than water.

17. A process as claimed in claim 14 which comprises mixing one part by volume of each of:

(i) the Extract 1;

(ii) the Extract 2; and (iii) the Extract 3.

18. A process as claimed in claim 14 which comprises mixing one part by volume of each of:

(i) 10 to 40% w/w of the Extract 1;

(ii) 10 to 40% w/w of the Extract 2, wherein a ratio of the second polar solvent to the water in the mixture of the second polar solvent and the water ranges from 20:80% w/w to 80:20% w/w; and (iii) 10 to 40% w/w of the Extract 3.

19. A process as claimed in claim 14 which comprises mixing one part by volume of each of:

(i) 20 to 30% w/w of the Extract 1;

(ii) 20 to 40% w/w of the Extract 2, wherein a ratio of the second polar solvent to the water in the mixture of the second polar solvent and the water ranges from 80:20% w/w to 20:80% w/w; and (iii) 20 to 30% w/w of the Extract 3; and wherein the pharmaceutical formulation further comprises one part by volume of:

(iv) 20 to 40% w/w of an Extract 4, wherein the Extract 4 is an extract of the plant *Phyllanthus amarus* obtained by using a second mixture of a third polar solvent and water alone, wherein a ratio of the third polar solvent to the water in the second mixture ranges from 20:80% w/w to 80:20% w/w, and wherein the third polar solvent comprises a polar solvent other than water.

20. A process as claimed in claim 14 which comprises mixing two parts by volume of:

(i) the Extract 1; and one part by volume of each of:

(ii) the Extract 2; and (iii) the Extract 3.

21. A process as claimed in claim 14 which comprises mixing two parts by volume of:
  (i) 10 to 40% w/w of the Extract 1; and
one part by volume of each of:
  (ii) 10 to 40% w/w of the Extract 2, wherein a ratio of the second polar solvent to the water in the mixture of the second polar solvent and the water ranges from 20:80% w/w to 80:20% w/w; and
  (iii) 10 to 40% w/w of the Extract 3.

22. A process as claimed in claim 14 which comprises mixing two parts by volume of:
  (i) 20 to 30% w/w of the Extract 1; and
one part by volume of each of:
  (ii) 20 to 40% w/w of the Extract 2, wherein a ratio of the second polar solvent to the water in the mixture of the second polar solvent and the water ranges from 80:20% w/w to 20:80% w/w; and
  (iii) 20 to 30% w/w of the Extract 3; and
wherein the pharmaceutical formulation further comprises one part by volume of:
  (iv) 20 to 40% w/w of an Extract 4, wherein the Extract 4 is an extract of a fourth amount of the plant Phyllanthus amarus obtained by using a second mixture of a third polar solvent and water alone, wherein a ratio of the third polar solvent to the water in the second mixture ranges from 20:80% w/w to 80:20% w/w, and wherein the third polar solvent comprises a polar solvent other than water.

23. A process as claimed in claim 14 wherein the extracts are prepared from powder obtained by:
  drying parts of taxonomically identified collections of the plant *Phyllanthus amarus;*
  keeping the dried parts in an oven heated to a temperature of 50 to 80 degrees C for 3 to 5 hours a day for a period of 3 to 6 successive days; and
  powdering the dried parts.

24. A process as claimed in claim 23 wherein before subjecting the powder to extraction procedures, each batch of powder is subjected to an optional sterilizing treatment to remove any bacterial or fungal contamination.

25. A process as claimed in claim 14 wherein extraction is carried out at a temperature in a range of 37 to 60 degrees C. for a period ranging from 2 hours to 18 hours.

26. A process as claimed in claim 14 wherein the polar solvent that is used for extraction comprises methanol, ethanol, butanol, or mixtures thereof.

27. A process as claimed in claim 23, wherein the parts are selected from the group consisting of leaves, stems, seeds, roots, and mixtures thereof.

28. A process as claimed in claim 14 which comprises mixing:
  (i) 20 to 30% w/w of the Extract 1;
  (ii) 20 to 40% w/w of the Extract 2, wherein a ratio of the second polar solvent to the water in the mixture of the second polar solvent and the water ranges from 80:20% w/w to 20:80% w/w; and
  (iii) 20 to 30% w/w of the Extract 3.

29. A process as claimed in claim 14 which comprises mixing one part by volume of each of:
  (i) 20 to 30% w/w of the Extract 1;
  (ii) 20 to 40% w/w of the Extract 2, wherein a ratio of the second polar solvent to the water in the mixture of the second polar solvent and the water ranges from 80:20% w/w to 20:80% w/w; and
  (iii) 20 to 30% w/w of the Extract 3.

30. A process as claimed in claim 14 which comprises mixing two parts by volume of:
  (i) 20 to 30% w/w of the Extract 1; and
one part by volume of each of:
  (ii) 20 to 40% w/w of the Extract 2, wherein a ratio of the second polar solvent to the water in the mixture of the second polar solvent and the water ranges from 80:20% w/w to 20:80% w/w; and
  (iii) 20 to 30% w/w of the Extract 3.

* * * * *